United States Patent
Ostermeier et al.

(10) Patent No.: US 11,147,814 B2
(45) Date of Patent: *Oct. 19, 2021

(54) (4-((3R,4R)-3-METHOXYTETRAHYDRO-PYRAN-4-YLAMINO)PIPERIDIN-1-YL) (5-METHYL-6-(((2R,6S)-6-(P- TOLYL) TETRAHYDRO-2H-PYRAN-2-YL) METHYLAMINO)PYRIMIDIN-4-YL) METHANONE CITRATE

(71) Applicant: Centrexion Therapeutics Corporation, Boston, MA (US)

(72) Inventors: Markus Ostermeier, Ingelheim am Rhein (DE); Ulrike Werthmann, Ingelheim am Rhein (DE)

(73) Assignee: Centrexion Therapeutics Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/787,433

(22) Filed: Feb. 11, 2020

(65) Prior Publication Data

US 2020/0276197 A1    Sep. 3, 2020

Related U.S. Application Data

(63) Continuation of application No. 16/224,902, filed on Dec. 19, 2018, now Pat. No. 10,568,885, which is a continuation of application No. 15/849,929, filed on Dec. 21, 2017, now Pat. No. 10,213,428, which is a continuation of application No. PCT/US2016/040728, filed on Jul. 1, 2016.

(30) Foreign Application Priority Data

Jul. 2, 2015   (EP) ................................ 15175066

(51) Int. Cl.
| | |
|---|---|
| A61K 31/506 | (2006.01) |
| A61K 31/166 | (2006.01) |
| A61K 31/351 | (2006.01) |
| A61K 31/4545 | (2006.01) |
| C07D 405/14 | (2006.01) |
| A61P 29/00 | (2006.01) |

(52) U.S. Cl.
CPC .......... *A61K 31/506* (2013.01); *A61K 31/166* (2013.01); *A61K 31/351* (2013.01); *A61K 31/4545* (2013.01); *A61P 29/00* (2018.01); *C07D 405/14* (2013.01)

(58) Field of Classification Search
CPC .. A61K 31/506; A61K 31/166; A61K 31/351; A61K 31/4545; C07D 405/14
USPC ...................................................... 514/256
See application file for complete search history.

(56) References Cited

U.S. PATENT DOCUMENTS

| | | |
|---|---|---|
| 4,032,526 A | 6/1977 | Cross et al. |
| 5,096,916 A | 3/1992 | Skupin |
| 5,629,235 A | 5/1997 | Liu |
| 5,629,325 A | 5/1997 | Lin et al. |
| 5,631,269 A | 5/1997 | Broughton et al. |
| 6,127,386 A | 10/2000 | Lin et al. |
| 6,143,892 A | 11/2000 | Graneto et al. |
| 6,423,713 B1 | 7/2002 | Anantanarayan et al. |
| 6,437,138 B1 | 8/2002 | Lin et al. |
| 6,514,977 B1 | 2/2003 | Anantanarayan et al. |
| 6,806,279 B2 | 10/2004 | Arkin et al. |
| 6,979,686 B1 | 12/2005 | Naraian et al. |
| 7,504,511 B2 | 3/2009 | Carayon et al. |
| 7,507,740 B2 | 3/2009 | Ishikawa et al. |
| 7,612,201 B2 | 11/2009 | Beswick et al. |
| 7,777,041 B2 | 8/2010 | Carayon et al. |
| 7,807,671 B2 | 10/2010 | Wang et al. |
| 7,891,384 B2 | 2/2011 | Binet et al. |
| 7,915,261 B2 | 3/2011 | Ishii et al. |
| 7,919,494 B2 | 4/2011 | Ishii et al. |
| 7,919,495 B2 | 4/2011 | Ishii et al. |
| 8,048,899 B2 | 11/2011 | Bartolozzi et al. |
| 8,110,575 B2 | 2/2012 | Gottschling et al. |
| 8,288,540 B2 | 10/2012 | Chianelli et al. |
| 8,329,735 B2 | 12/2012 | Ermann et al. |
| 8,349,871 B2 | 1/2013 | Bartolozzi et al. |
| 8,362,039 B2 | 1/2013 | Bartolozzi et al. |
| 8,765,949 B2 | 7/2014 | Ebel et al. |
| 8,835,440 B2 | 9/2014 | Ebel et al. |
| 8,841,313 B2 | 9/2014 | Ebel et al. |
| 8,962,656 B2 | 2/2015 | Ebel et al. |
| 9,067,951 B2 | 6/2015 | Ebel et al. |
| 9,670,222 B2 * | 6/2017 | Ebel .................. A61P 13/12 |
| 10,196,402 B2 | 2/2019 | Ebel et al. |

(Continued)

FOREIGN PATENT DOCUMENTS

| | | |
|---|---|---|
| CA | 2687931 A1 | 12/2008 |
| CA | 2704883 A1 | 5/2009 |

(Continued)

OTHER PUBLICATIONS

Cannon, J.G., Chapter Nineteen in Burger's Medicinal Chemistry and Drug Discovery, Fifth Edition, vol. I: Principles and Practice, Wiley-Interscience 1995, pp. 783-802, 784.

Sheridan, R. P. "The Most Common Chemical Replacements in Drug-Like Compounds" *J. Chem. Inf. Comput. Sci.*, 2002, vol. 42, pp. 103-108.

(Continued)

*Primary Examiner* — Yevgeny Valenrod
(74) *Attorney, Agent, or Firm* — Dechert LLP

(57) ABSTRACT

The invention provides a salt of a tetrahydropyranylmethylaminopyrimidine amide, such as the citrate salt of (4-((3R,4R)-3-methoxytetrahydropyran-4-ylamino)piperidin-1-yl) (5-methyl-6-(((2R,6S)-6-(p-tolyl)tetrahydro-2H-pyran-2-yl) methylamino)pyrimidin-4-yl)methanone, pharmaceutical compositions containing the same, processes for preparing the same, and methods of medical treatment using the same.

20 Claims, 18 Drawing Sheets

(56) References Cited

U.S. PATENT DOCUMENTS

| | | | |
|---|---|---|---|
| 10,213,428 B2* | 2/2019 | Ostermeier | A61K 31/506 |
| 10,568,885 B2* | 2/2020 | Ostermeier | A61K 31/166 |
| 2003/0195195 A1 | 10/2003 | Haviv et al. | |
| 2004/0014744 A1 | 1/2004 | Haviv et al. | |
| 2004/0147561 A1 | 7/2004 | Zhong et al. | |
| 2004/0167156 A1 | 8/2004 | Jiao et al. | |
| 2004/0220171 A1 | 11/2004 | Pauls et al. | |
| 2005/0192302 A1 | 9/2005 | Xue et al. | |
| 2005/0222151 A1 | 10/2005 | Carruthers et al. | |
| 2005/0245537 A1 | 11/2005 | Tsuchimori et al. | |
| 2006/0004049 A1 | 1/2006 | Yao et al. | |
| 2006/0030557 A1 | 2/2006 | Haviv et al. | |
| 2006/0173012 A1 | 8/2006 | Hohlweg | |
| 2007/0032475 A1 | 2/2007 | Ye et al. | |
| 2007/0032489 A1 | 2/2007 | Weintraub et al. | |
| 2007/0244132 A1 | 10/2007 | Ishikawa et al. | |
| 2007/0281936 A1 | 12/2007 | Gillespie et al. | |
| 2008/0161280 A1 | 7/2008 | Gandhi et al. | |
| 2008/0306046 A1 | 12/2008 | Ishii et al. | |
| 2009/0048238 A1 | 2/2009 | Aebi et al. | |
| 2009/0131417 A1 | 5/2009 | Letavic et al. | |
| 2009/0318467 A1 | 12/2009 | Adam et al. | |
| 2010/0009971 A1 | 1/2010 | Ishii et al. | |
| 2010/0009972 A1 | 1/2010 | Ishii et al. | |
| 2010/0204209 A1 | 8/2010 | Ebel et al. | |
| 2010/0204230 A1 | 8/2010 | Blurton et al. | |
| 2011/0021500 A1 | 1/2011 | Gottschling et al. | |
| 2011/0183957 A1 | 7/2011 | Wityak et al. | |
| 2011/0195954 A1 | 8/2011 | Gottschling et al. | |
| 2011/0301143 A1 | 12/2011 | Isabel et al. | |
| 2012/0004252 A1 | 1/2012 | Ebel et al. | |
| 2012/0053164 A1 | 3/2012 | Ebel et al. | |
| 2012/0088754 A1 | 4/2012 | Van Emelen et al. | |
| 2012/0108572 A1 | 5/2012 | Wagner et al. | |
| 2013/0090338 A1 | 4/2013 | Ebel et al. | |
| 2013/0123241 A1 | 5/2013 | Ebel et al. | |
| 2013/0143905 A1 | 6/2013 | Ebel et al. | |
| 2013/0150354 A1 | 6/2013 | Ebel et al. | |
| 2013/0172348 A1 | 7/2013 | Ebel et al. | |
| 2013/0184299 A1 | 7/2013 | Ebel et al. | |
| 2013/0217728 A1 | 8/2013 | Ebel et al. | |
| 2013/0324517 A1 | 12/2013 | Ebel et al. | |
| 2014/0235661 A1 | 8/2014 | Ebel et al. | |
| 2017/0362249 A1 | 12/2017 | Ebel et al. | |
| 2019/0262339 A1 | 8/2019 | Ostermeier et al. | |

FOREIGN PATENT DOCUMENTS

| | | |
|---|---|---|
| CA | 2705405 A1 | 5/2009 |
| EP | 1752457 A1 | 2/2007 |
| EP | 1849773 A1 | 10/2007 |
| EP | 2342199 A2 | 7/2011 |
| FR | 2854158 A1 | 10/2004 |
| GB | 2068961 A | 8/1981 |
| JP | 6229575 | 8/1994 |
| JP | 2003240776 A | 8/2003 |
| JP | 2007500135 A | 1/2007 |
| JP | 2008239617 A | 10/2008 |
| WO | WO-8606719 A1 | 11/1986 |
| WO | WO-9724324 A1 | 7/1997 |
| WO | WO-9921834 A1 | 5/1999 |
| WO | WO-0059502 A1 | 10/2000 |
| WO | WO-0066558 A1 | 11/2000 |
| WO | WO-0190101 A1 | 11/2001 |
| WO | WO-03037271 A2 | 5/2003 |
| WO | WO-03051797 A2 | 6/2003 |
| WO | WO-03066604 A2 | 8/2003 |
| WO | WO-03074500 A2 | 9/2003 |
| WO | WO-03092586 A2 | 11/2003 |
| WO | WO-03104223 A1 | 12/2003 |
| WO | WO-2004024710 A1 | 3/2004 |
| WO | WO-2004074438 A2 | 9/2004 |
| WO | WO-2004080976 A1 | 9/2004 |
| WO | WO-2004101546 A1 | 11/2004 |
| WO | WO-2005009976 A1 | 2/2005 |
| WO | WO-2005014571 A1 | 2/2005 |
| WO | WO-2005060665 A2 | 7/2005 |
| WO | WO-2005084667 A1 | 9/2005 |
| WO | WO-2005097751 A2 | 10/2005 |
| WO | WO-2005117909 A2 | 12/2005 |
| WO | WO-2005118588 A1 | 12/2005 |
| WO | WO-2006001958 A2 | 1/2006 |
| WO | WO-2006003277 A1 | 1/2006 |
| WO | WO-2006004741 A2 | 1/2006 |
| WO | WO-2006012135 A1 | 2/2006 |
| WO | WO-2006021801 A1 | 3/2006 |
| WO | WO-2006029906 A1 | 3/2006 |
| WO | WO-2006034440 A2 | 3/2006 |
| WO | WO-2006034833 A1 | 4/2006 |
| WO | WO-2006038734 A1 | 4/2006 |
| WO | WO-2006050389 A2 | 5/2006 |
| WO | WO-2006072350 A1 | 7/2006 |
| WO | WO-2006073592 A2 | 7/2006 |
| WO | WO-2006088075 A1 | 8/2006 |
| WO | WO-2006/113261 A2 | 10/2006 |
| WO | WO-2006113704 A2 | 10/2006 |
| WO | WO-2007003604 A2 | 1/2007 |
| WO | WO-2007016496 A2 | 2/2007 |
| WO | WO-2007022937 A1 | 3/2007 |
| WO | WO-2007026959 A2 | 3/2007 |
| WO | WO-2007030061 A1 | 3/2007 |
| WO | WO-2007038669 A2 | 4/2007 |
| WO | WO-2007048779 A1 | 5/2007 |
| WO | WO-2007053495 A2 | 5/2007 |
| WO | WO-2007053498 A1 | 5/2007 |
| WO | WO-2007071358 A1 | 6/2007 |
| WO | WO-2007074438 A2 | 7/2007 |
| WO | WO-2007084786 A1 | 7/2007 |
| WO | WO-2007084868 A2 | 7/2007 |
| WO | WO-2007092065 A2 | 8/2007 |
| WO | WO-2007100851 A1 | 9/2007 |
| WO | WO-2007105058 A2 | 9/2007 |
| WO | WO-2007120574 A2 | 10/2007 |
| WO | WO-2007127448 A2 | 11/2007 |
| WO | WO-2007147874 A1 | 12/2007 |
| WO | WO-2008014199 A2 | 1/2008 |
| WO | WO-2008029084 A1 | 3/2008 |
| WO | WO-2008039645 A1 | 4/2008 |
| WO | WO-2008060621 A2 | 5/2008 |
| WO | WO-2008083027 A1 | 7/2008 |
| WO | WO-2008145681 A2 | 12/2008 |
| WO | WO-2008145861 A2 | 12/2008 |
| WO | WO-2009003861 A1 | 1/2009 |
| WO | WO-2009013211 A2 | 1/2009 |
| WO | WO-2009026204 A1 | 2/2009 |
| WO | WO-2009043747 A2 | 4/2009 |
| WO | WO-2009048238 A2 | 4/2009 |
| WO | WO-2009065919 A2 | 5/2009 |
| WO | WO-2009065920 A2 | 5/2009 |
| WO | WO-2009066084 A1 | 5/2009 |
| WO | WO-2009153182 A1 | 12/2009 |
| WO | WO-2010017179 A1 | 2/2010 |
| WO | WO-2010020432 A2 | 2/2010 |
| WO | WO-2010036630 A2 | 4/2010 |
| WO | WO-2010036631 A2 | 4/2010 |
| WO | WO-2010070032 A1 | 6/2010 |
| WO | WO-2011073154 A1 | 6/2011 |
| WO | WO-2011073155 A1 | 6/2011 |
| WO | WO-2011109324 A1 | 9/2011 |
| WO | WO-2011141474 A1 | 11/2011 |
| WO | WO-2011141477 A1 | 11/2011 |
| WO | WO-2011144501 A1 | 11/2011 |
| WO | WO-2011147772 A1 | 12/2011 |
| WO | WO-2011151251 A1 | 12/2011 |
| WO | WO-2012171863 A1 | 12/2012 |
| WO | WO-2013010839 A1 | 1/2013 |

OTHER PUBLICATIONS

Chemical Abstracts Service, Columbus, OH, US, Yamashita, Hiroshi et al: "Preparation of benzothiophenylpiperazine derivatives for treatment of central nervous system diseases", XP002528684 retrieved from STN. Database accession No. 2008:1217060,Compound RN:

(56) References Cited

OTHER PUBLICATIONS 928251-63-2 *abstract* & JP 2008 239617 A (Ohtsuka Pharmaceutical Co., Ltd, Japan) Oct. 9, 2008.
Chemical Abstracts Service, Columbus, OH; US; Ledeboer; Mark W. et al: "Pyrrolopyridines useful as inhibitors of protein kinase and their preparation, pharmaceutical compositions, and use in the treatment of various diseases", XP002528685 retrieved from STN, Database accession No. 2006:1252802 Compounds RN: 916172-93-5, 916172-95-7 *abstract* & WO 2006/127587 AI (Vertex Pharmaceuticals Incorporated; USA) Nov. 30, 2006.
Cuzzocrea, S. "Shock, Inflammation and PARP", Pharmacological Research (2005) vol. 52 pp. 72-82.
Barril, Xavier, et al; 4-Amino Derivates of the Hsp90 Inhibitor CCT018159; Bioorganic & Medicinal Chemistry Letters (2006) vol. 16 p. 2543-2548.
Carter, Percy H., et al. "Advances in the Discovery of CC Chemokine Receptor 2 Antagonists", Annual Reports in Medicinal Chemistry (2007) vol. 42 pp. 211-228.
Chabner, Bruce, A., et al; Chemotherapy of Neoplastic Diseases: Antineoplastic Agents: Goodman & Gilman's: The Pharmacological Basis of Therapeutics by Laurence L. Brunton et al (2006) 11th Ed. pp. 1315-1403.
Chemical Abstracts Service, Columbus, OH, US, STN Database, Compound Registration No. 837395-83-2, entered STN Feb. 25, 2005.
Chemical Abstracts Service, Columbus, OH, US, STN Database, Compound Registration No. 837396-47-1, entered STN on Feb. 25, 2005.
Donnelly, L. E. and Barnes, P. J. "Chemokine Receptors as Therapeutic Targets in Chronic Obstructive Pulmonary Disease," *Trends in Pharmacological Sciences* (2006) vol. 27, No. 10, pp. 546-553.
Hu, Wenhui, et al. "Development of a Novel Therapeutic Suppressor of Brain Proinflammatory Cytokine Up-Regulation that Attenuates Synaptic Dysfunction and Behavioral Deficits," *Bioorganic & Medicinal Chemistry Letters* (2007) vol. 17, pp. 414-418.
International Preliminary Report on Patentability for PCT/EP2009/067378 dated Jun. 21, 2011.
International Preliminary Report on Patentability for PCT/EP2010/069549 dated Jun. 19, 2012.
International Search Report for PCT/EP2008/056573 dated Jan. 14, 2009.
International Search Report for PCT/EP2009/067378 dated Apr. 16, 2010.
International Search Report for PCT/EP2010/069549 dated Feb. 23, 2011.
International Search Report for PCT/EP2010/069550 dated Feb. 23, 2011.
International Search Report for PCT/EP2011/057539 dated Jul. 20, 2011.
International Search Report for PCT/EP2011/057545 dated Jul. 4, 2011.
International Search Report for PCT/EP2011/057550 dated Jun. 28, 2011.
International Search Report for PCT/EP2011/058355 dated Aug. 9, 2011.
International Search Report for PCT/EP2011/058668 dated Jun. 28, 2011.
Kuettel, Sabine, et al. "Synthesis and Evaluation of Antiparasitic Activities of New 4-[5-(4-Phenoxyphenyl)-2H-pyrazol-3-yl]morpholine Derivatives," *Journal Med. Chem.* (2007) vol. 50, pp. 5833-5839.
Lagu, Bharat, et al. "Potent and Selective CC-Chemokine Receptor-2 (CCR2) Antagonists as a Potential Treatment for Asthma," *Bioorganic and Medicinal Chemistry Letters* (2007) vol. 17, pp. 4382-4386.
Poupaert, Jacques, H; Drug Design: Basic Principles and Applications; Encyclopedia of Pharmaceutical Technology (2007) 3rd edition pp. 1362-1369.
Xu, Ping, et al: Synthesis and Anticonvulsant Activity of 3-(Substituted piperazino)-6-(substituted phenyl) pyridazines; Chemical Abstracts Service (1991) vol. 23, No. 6, pp. 477-480.
Rival, Y. et al., "5-HT3 Antagonists Derived from Aminopyridazine-type Muscarinic M1 Agonists", Journal of Medicinal Chemistry, 1998, V.41, p. 311-317.
Castro, ME, et al., "Pyridazine derivatives XII. Synthesis and anti-psychotic-antidepressant activity of some butyrophenone derivatives of 6-phenylpyridazine", European Journal of Medicinal Chemistry, 1994, v. 29, p. 831-839.
E.A. Steck et al., "Some 6-Aryl-3-(basically-substituted) Pyridazines", Journal of Heterocyclic Chemistry, 1975, v. 12, No. 5, p. 1009-1013.
Refaat, H. and Omar, A. H., "Bulletin of the Faculty of Pharmacy", (Cairo University) Database CAPlus on STN, Entered STN 2005, vol. 42, No. 2, p. 415-423.
Hawtin, S. R. et al., "A Gly/Ala switch contributes to high affinity bonding of benzoxazinone-based non-peptide oxytocin receptor antagonists," (2005) *FEBS Letters*, vol. 579, p. 349-356.
Barnes, P. J. "New Treatments for COPD", Nature Rev. Drug Disc. 2002, p. 437-446.
Mar., Advanced Organic Chemistry Reactions, Mechanisms and Structure 641-678 (4th ed., 1992).
Rowley, M., et al. "4-Heterocyclylpiperidines as Selective High-Affinity Ligands at the Human Dopamine D4 Receptor," *J. Med. Chem.* (1997) vol. 40, pp. 2374-2385.
Xia, M. and Siu, Z. "Recent Developments in CCR2 antagonists," *Expert Opinion in Therapeutic Patents*, vol. 19, 2009, p. 295-303.
Abbadie, et al., 100 PNAS "Impaired neuropathic pain responses in mice lacking the chemokine receptor CCR2", p. 7947-7952 (2003).
Havlioglu, et al., "Slit Proteins, Potential Endogenous Modulators of Inflammation", *Neurovirology*, 8, p. 786-495, 2002. (Abstract Only).
Dray, A. "Neuropathic pain: emerging treatments," *Brit. J. Anaesthesia*, vol. 101, Issue 1, pp. 48-58 (2008).
Dansereau, et al., "Spinal CCL2 pronociceptive action is no longer effective in CCR2 receptor antagonist-treated rats," *J. Neurochem.* vol. 106, p. 757-769 (2008).
Buntinx, M. et al. "Pharmacological Profile of JNJ-27141491 [(S)-3[3,4-Difluorophenyl)-propyl]-5-isoxazol-5-yl-2-thioxo-2,3-dihydro-1H-imidazole-4-carboxyl Acid Methyl Ester], as a Noncompetitive and Orally Active Antagonist of the Human Chemokine Receptor CCR2," *J. Pharmacol. Experimental Therapeutics*, vol. 327, No. 1, p. 1-9 (2008).
Abbadie, C. et al. "Chemokines and pain mechanisms," *Brain Res. Rev.* vol. 60, p. 125-134 (2009).
Jung, H. et al. "Activation of the nuclear factor of activated T-cells (NFAT) mediates upregulation of CCR2 chemokine receptors in dorsal root ganglion (DRG) neurons: A possible mechanism for activity-dependent transcription in DRG neurons in association with neuropathic pain" *Mol. Cell. Neurosci.* vol. 37, No. 1, p. 170-177 (2008).
Jung, H. et al. "Visualization of Chemokine Receptor Activation in Transgenic Mice Reveals Peripheral Activation of CCR2 Receptors in States of Neuropathic Pain" *J. Neurosci.* vol. 29 p. 8051-8062 (2009).
Hunskaar, S. et al. "The formalin test in mice: dissociation between inflammatory and non-inflammatory pain" *Pain*, vol. 30, p. 103-114, (1987). (Abstract Only).
White, F. A. "Chemokine Signaling and the Management of Neuropathic Pain" *Molecular Interventions*, vol. 9, p. 188-195 (2009).
White, F. A. & Wilson, N. "Chemokines as Pain Mediators and Modulators" *Curr. Opin. Anaesthesiol.* vol. 21, p. 580-585 (2008).
Serrano, A. et al. "Blocking spinal CCR2 with AZ889 reversed hyperalgesia in a model of neuropathic pain" *Molecular Pain*, 6:90 (2010).
Zhang, J. et al. "Expression of CCR2 in Both Resident and Bone Marrow-Derived Microglia Plays a Critical Role in Neuropathic Pain" *J. Neurosci.* vol. 27, p. 12396-12406 (2007).
Xia, M. et al. "Synthesis, Structure-Activity Relationship and in Vivo Antiinflammatory Efficacy of Substituted Dipiperidines as CCR2 Antagonists" *J. Med. Chem.* vol. 50, p. 5561-5563 (2007).

(56) References Cited

OTHER PUBLICATIONS

Jerath, M. R. et al. "Dual targeting of CCR2 and CX3CR1 in an arterial injury model of vascular inflammation" *Thromb. J.* 8:14 (2010).

Min, S. H. et al. "Pharmacological targeting reveals distinct roles for CXCR2/CXCR1 and CCR2 in a mouse model of arthritis." *Biochem. Biophys. Res. Comm.* vol. 391, p. 1080-1086 (2010). (Abstract Only).

Lee, Y. et al. "In vivo MR evaluation of the effect of the CCR2 antagonist on macrophage migration" *Magnetic Resonance in Medicine*, vol. 64, p. 72-79 (2010).

Wisniewski, T. et al. "Assessment of chemokine receptor function on monocytes in whole blood: In vitro and ex vivo evaluations of a CCR2 antagonist." *J. Immunol. Methods*, vol. 352, p. 101-110 (2010). (Abstract Only).

Tominaga, T. et al. "Blocking Mast Cell-Mediated Type I Hypersensitivity in Experimental Allergic Conjunctivitis by Monocyte Chemoattractant protein-1/CCR2" *Investigative Ophthalmology & Visual Sci.* vol. 50, p. 5181-5188 (2009).

Kadl, A. "Induction of CCR2-dependent macrophage accumulation by oxidized phospholipids in the air-pouch model of inflammation." *Arthritis Rheum.* vol. 60, p. 1362-1371 (2009).

Sorensen, T. L. et al. "Chemokine CCL2 and chemokine receptor CCR2 in early active multiple sclerosis." *Eur. J. Neurol.* vol. 11, p. 445-449 (2004). (Abstract Only).

Kalinowska, A. et al. "Investigational C-C chemokine receptor 2 antagonists for the treatment of autoimmune diseases." *Expert Opin. Investig. Drugs*, vol. 17, p. 1267-1279 (2008). (Abstract Only).

Berge et al. in Journal of Pharmaceutical Sciences (1977) vol. 66(1), pp. 1-19.

International Search Report and Written Opinion for PCT/US2016/040728 dated Sep. 28, 2016. (7 pages).

Dario Braga et al. "Crystal Polymorphism and Multiple Crystal Forms" Struct Bond (2009) 132: pp. 25-50, XP55378617.

Extended European Search Report, EP Application No. 16818898.5, dated Dec. 3, 2018.

U.S. Appl. No. 16/233,315, CCR2 Receptor Antagonists and Uses Thereof, filed Dec. 27, 2018.

\* cited by examiner

(4-((3R,4R)-3-METHOXYTETRAHYDRO-PYRAN-4-YLAMINO)PIPERIDIN-1-YL) (5-METHYL-6-(((2R,6S)-6-(P- TOLYL) TETRAHYDRO-2H-PYRAN-2-YL) METHYLAMINO)PYRIMIDIN-4-YL) METHANONE CITRATE

CROSS REFERENCE TO RELATED APPLICATIONS

This application is a continuation of U.S. patent application Ser. No. 16/224,902, filed Dec. 19, 2018, which is a continuation of U.S. patent application Ser. No. 15/849,929, filed Dec. 21, 2017, now U.S. Pat. No. 10,213,428, which is a continuation of International Patent Application No. PCT/US2016/040728, filed Jul. 1, 2016, which claims the benefit of and priority to European Patent Application serial number 15175066.8, filed Jul. 2, 2015, the contents of each of which are hereby incorporated by reference in their entirety.

FIELD OF THE INVENTION

The present invention provides the citrate salt of (4-((3R,4R)-3-methoxytetrahydro-pyran-4-ylamino)piperidin-1-yl) (5-methyl-6-(((2R,6S)-6-(p-tolyl)tetrahydro-2H-pyran-2-yl)methylamino)pyrimidin-4-yl)methanone and to a process for manufacturing it. The present invention also provides the same citrate salt for use in the treatment of medical conditions, such as acute and chronic mild to moderate musculoskeletal pain, low back pain, chronic low back pain, pain related to rheumatoid arthritis, shoulder pain, dental pain, signs and symptoms of osteoarthritis, osteoarthritis of the knee, osteoarthritis of the hip, osteoarthritis of the hand, pain associated with osteoarthritis, cancer pain, diabetic polyneuropathy, visceral pain, acute pain, diabetic nephropathy, neuropathic pain, as well as to a pharmaceutical composition comprising the same salt.

BACKGROUND

WO 2011/073154 discloses a number of tetrahydropyranyl-methyl-amino-(hetero)aryl-amides without disclosing any specific salt or crystal form of the compounds exemplified therein. Among others, WO 2011/073154 discloses compound I

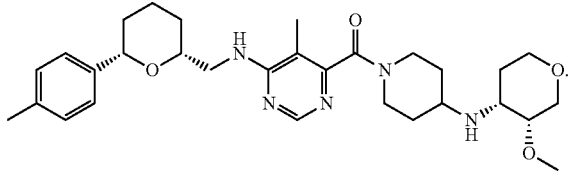

I

Compounds disclosed in WO 2011/073154 are potent CCR2 antagonists. However, in order to prove to be developable for use as a medicament in a human, a drug substance and its solid form must, in addition to in vitro and in vivo pharmacokinetic and pharmacological properties and safety profile, fulfil a series of criteria with regard to the requirements of chemistry, manufacturing and controls (CMC) such as solid form characteristics, purity, drying times, filterability, stability, thermal stability, hygroscopicity, reproducibility and further physicochemical properties including solubility and intrinsic dissolution rate.

One of the biggest challenges in the course of the development of a drug product for medical use in humans is to identify a drug substance which is potent, efficacious, fulfils safety requirements and simultaneously has a solid form suitable for human drug development, i.e., fulfilling all the above mentioned criteria cumulatively. This is because each and every solid form, salt and polymorphic form thereof has physicochemical and pharmacokinetic properties which are just as unforeseeable as unexpected.

Furthermore, due to the unpredictable and unexpected nature of the solid, salt and polymorphic forms, there is neither generic nor specific guidance for the skilled person how to design a solid form with the desired characteristics. Therefore, extensive and creative research and experimentation is essential to arrive at the specific solid form of a selected drug substance that fulfils all requirements. Optimization of one crucial parameter often results in the deterioration of another or other parameter(s).

SUMMARY

The objective technical problem underlying the present invention is to provide a drug substance with CCR2 antagonistic activity which is developable for use as a medicament in humans, i.e., where:
a) the drug substance is characterised by high pharmacological potency, efficacy, in vitro and in vivo pharmacokinetics, and necessary safety properties; and
b) the drug substance and its solid form fulfil a series of criteria with regard to the requirements of chemistry, manufacturing and controls (CMC) such as solid form characteristics, purity, drying times, filterability, stability, thermal stability, hygroscopicity, reproducibility and further physicochemical properties including solubility and intrinsic dissolution rate.

Compound I has surprisingly been found to fulfil the majority of the above mentioned criteria required for use as a medicament in humans as demonstrated (see biological data below). These parameters include plasma protein binding (relevant for pharmacokinetics and pharmacodynamics), in vitro metabolic stability (relevant for pharmacokinetics), pharmacokinetics and safety properties (hERG, relevant for cardiovascular safety, and drug-induced phospholipidosis).

However, the free base of compound I however turned out to be an amorphous material which was in a metastable state and thus subject to metamorphosis. It was not suitable as a drug substance for development because it did not fulfil the requirement of being able to be reproducibly manufactured.

Attempts to obtain compound I in crystalline form from solutions in all commonly used solvents such as ethanol, ethanol/water, 2-propanol, 2-propanol/water, acetone, ethyl acetate, 2-butanone or tetrahydrofuran failed. Such attempts to obtain compound I in crystalline form from solutions in all commonly used solvents such as ethanol, ethanol/water, 2-propanol, 2-propanol/water, acetone, ethyl acetate, 2-butanone or tetrahydrofuran yielded only amorphous material. Due to these failures, salt forms of compound I with various acids were investigated.

To ensure reproducibility of the physicochemical properties in the pharmaceutical manufacturing process, the drug substance must invariably be obtained in a well-defined crystalline modification. When a crystalline form of a drug substance or its salt exists in different polymorphic modifications (polymorphism), spontaneous conversion of one polymorphic form into another one may occur. Such a spontaneous interconversion cannot be tolerated and should be avoided by all means. Therefore, it is essential for securing the reproducibility of the pharmaceutical manufacturing process to identify a salt of a drug substance that exists either in one crystalline form only, or that at least is characterized by a reduced tendency towards polymorphism.

According to the present invention, the technical problem outlined above has been solved by experimentation and innovation that resulted in the identification of the specific compound (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate salt 1

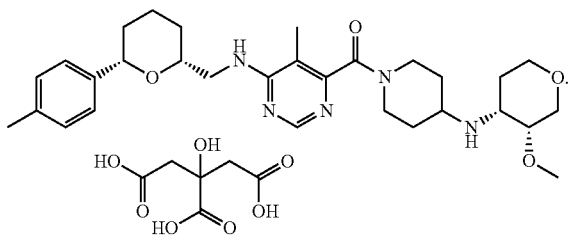

1

The citrate salt 1 is crystalline, i.e., defined by a specific crystal modification, thus allowing to obtain the drug substance in high purity and reproducibly high stability.

Various salt forms of compound I where prepared and analysed. For instance, crystalline forms of the citrate, hydrobromide, hydrochloride, esilate and methanesulfonate salt of compound I were obtained by crystallization. Analysis of these salt forms unexpectedly revealed that the citrate, esilate and methanesulfonate salts of compound I exhibited only one polymorphic form. This stands in contrast to the hydrobromide and hydrochloride salts of compound I, which were obtained in different polymorphic modifications.

Another key parameter of a drug substance is hygroscopicity. Water uptake of a salt of a drug substance by sorption during manufacture leads to a reduced amount of the drug substance in the drug product and therefore to reduced efficacy. In addition, water uptake of a salt of a drug substance or a drug product may lead to decomposition of the drug substance. Therefore, it is essential to identify a drug substance or salt thereof that is not hydroscopic, or has only very little hygroscopic character.

Unexpectedly, the crystalline form of the citrate salt 1 of compound I is characterized by low and reversible water uptake at a relative humidity of up to 90% (2.6% water uptake at 80% relative humidity and 3.4% water uptake at 90% relative humidity). On the contrary, the crystalline forms of the corresponding hydrobromide, hydrochloride, esilate and methanesulfonate of compound I readily absorb significant amounts of water at a relative humidity of as low as 80% and become irreversibly deliquescent.

Accordingly, one aspect of the invention provides the compound having the following formula 1:

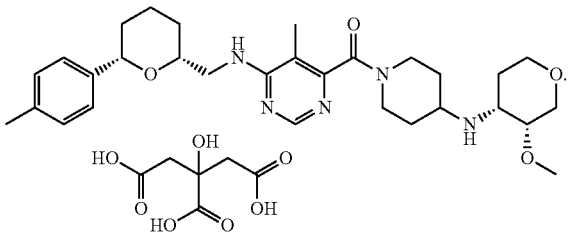

1

In certain embodiments, the compound is provided in crystalline form.

Another aspect of the invention provides a pharmaceutical composition comprising (i) a compound described herein such as citrate salt 1 and (ii) one or more carriers and/or diluents. In certain embodiments, the pharmaceutical composition is formulated for oral administration.

Another aspect of the invention provides the citrate salt 1 or a pharmaceutical composition comprising said citrate salt 1 for use in treating a medical condition. Exemplary medical conditions include, for example, treatment of pain (e.g., inflammatory pain or neuropathic pain) and osteoarthritis.

Another aspect of the invention provides a method of treating a medical condition in a patient, where the method comprises administering to a patient in need thereof a therapeutically effective amount of a compound described herein, such as citrate salt 1, in order to treat the medical condition. Exemplary medical conditions include, for example, pain (e.g., inflammatory pain or neuropathic pain) and osteoarthritis.

DETAILED DESCRIPTION

Figure 1:
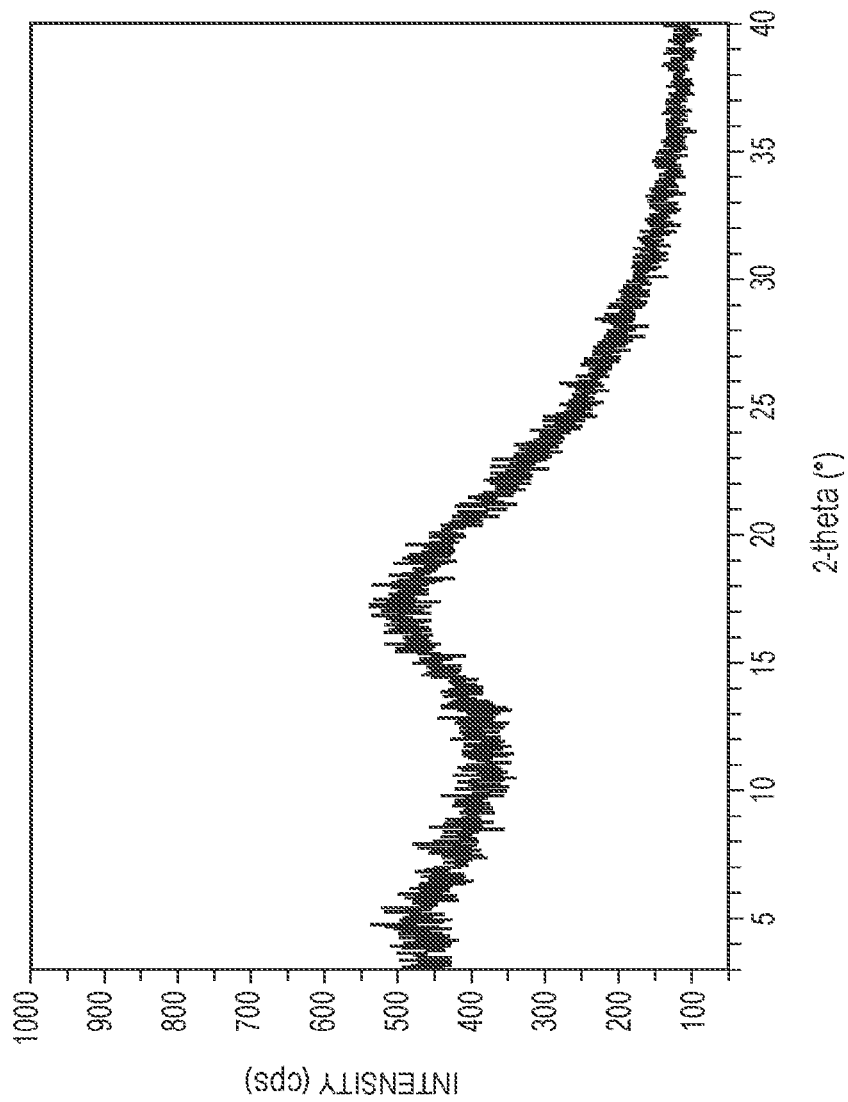
FIG. 1 shows the X-ray powder diffractogram of the amorphous base of the compound (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone.

The invention provides salt forms of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone, pharmaceutical compositions containing such salt forms, methods for preparing salt forms, and therapeutic methods for using such salt forms, such as in the treatment of pain and other medical conditions. As described herein, the citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone was surprisingly discovered to provide multiple unexpected benefits over other salt forms of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone. For example, the citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone was found to exhibit low and reversible water uptake at a relative humidity up to 90%, which stands in contrast to salt forms of the corresponding hydrobromide, hydrochloride, esilate, and methanesulfonate that readily absorb significant amounts of water at a relative humidity of as low as 80% and become irreversibly deliquescent. Further still, the citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone was unexpectedly found to exhibit only one polymorphic crystalline form, which stands in contrast to the corresponding crystalline salts formed from hydrobromic acid and hydrochloric acid that exhibited different polymorphic modifications. Accordingly, the citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone is surprisingly superior for development as a pharmaceutical due to the multiple unexpected properties that are beneficial.

Various aspects and embodiments of the invention are further described below in sections. Aspects and embodiments of the invention described in one particular section are not to be limited to any particular section.

To facilitate an understanding of the present invention, a number of terms and phrases are defined below.

The terms "subject" and "patient" refer to organisms to be treated by the methods of the present invention. Such organisms include mammals (e.g., murines, simians, equines, bovines, porcines, canines, felines, and the like), and most preferably is humans.

The term "effective amount" refers to the amount of a compound sufficient to effect beneficial or desired results. An effective amount can be administered in one or more administrations, applications or dosages and is not intended to be limited to a particular formulation or administration route.

The term "treating" includes any effect, e.g., lessening, reducing, modulating, ameliorating or eliminating, that results in the improvement of the condition, disease, disorder, and the like, or ameliorating a symptom thereof.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

I. Salt Forms of 4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone One aspect of the invention provides salt forms of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone. As described below and in the working examples, this disclosure describes salt forms of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone prepared by reacting 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)

methylamino)pyrimidin-4-yl)methanone with an acid selected from citric acid, hydrobromic acid, hydrochloric acid, ethanesulfonic acid, and methanesulfonic acid.

The citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone was surprisingly discovered to provide multiple unexpected benefits over other salt forms of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone. For example, the citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone was found to exhibit low and reversible water uptake at a relative humidity up to 90%, which stands in contrast to salt forms of the corresponding hydrobromide, hydrochloride, esilate, and methanesulfonate that readily absorb significant amounts of water at a relative humidity of as low as 80% and become irreversibly deliquescent. Further still, the citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone was unexpectedly found to exhibit only one polymorphic crystalline form, which stands in contrast to the corresponding crystalline salts formed from hydrobromic acid and hydrochloric acid that exhibited different polymorphic modifications. Accordingly, the citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone is surprisingly superior for development as a pharmaceutical due to the multiple unexpected properties that are beneficial.

Accordingly, one aspect of the invention provides the citrate salt of compound I:

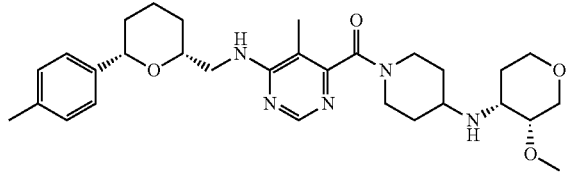

I having the formula

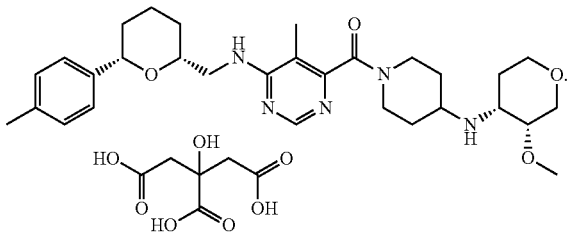

1

In certain embodiments, said citrate salt is in crystalline form.

In certain embodiments, the crystalline form is characterized by showing a X-ray powder diffraction pattern comprising peaks at the following 2-theta values measured using monochromatic CuKα1 radiation of λ=1.54056 Å, 40 kV, 40 mA: 19.1° and 22.4°. In certain embodiments, the crystalline form is characterized in that the X-ray powder diffraction pattern further comprises a peak at 12.2°. In certain embodiments, the crystalline form is characterized in that the X-ray powder diffraction pattern further comprises a peak at 13.7°. In certain embodiments, the crystalline form is characterized in that the X-ray powder diffraction pattern further comprises a peak at 14.6°. In certain embodiments, the crystalline form is characterized in that the X-ray powder diffraction pattern further comprises a peak at 18.7°. In certain embodiments, the crystalline form is characterized in that the X-ray powder diffraction pattern further comprises a peak at 24.6°. In certain embodiments, the crystalline form is characterized in that X-ray powder diffraction pattern further comprises a peak at 26.3°.

In certain embodiments, the crystalline form exhibits a X-ray powder diffraction pattern comprising peaks at the following 2-theta values measured using monochromatic CuKα1 radiation of λ=1.54056 Å, 40 kV, 40 mA: 12.2±0.2, 13.7±0.2, 14.6±0.2, 19.1±0.2, and 22.4±0.2. In certain other embodiments, the crystalline form exhibits a X-ray powder diffraction pattern comprising peaks at the following 2-theta values measured using monochromatic CuKα1 radiation of λ=1.54056 Å, 40 kV, 40 mA: 12.2±0.2, 13.7±0.2, 14.6±0.2, 18.7±0.2, 19.1±0.2, 22.4±0.2, 24.6±0.2, and 26.3±0.2.

In certain embodiments, the relative intensity of the peak at said diffraction angles 2-theta is at least 10%. In certain other embodiments, the relative intensity of the peak at said diffraction angles 2-theta is at least 15%.

Figure 2:
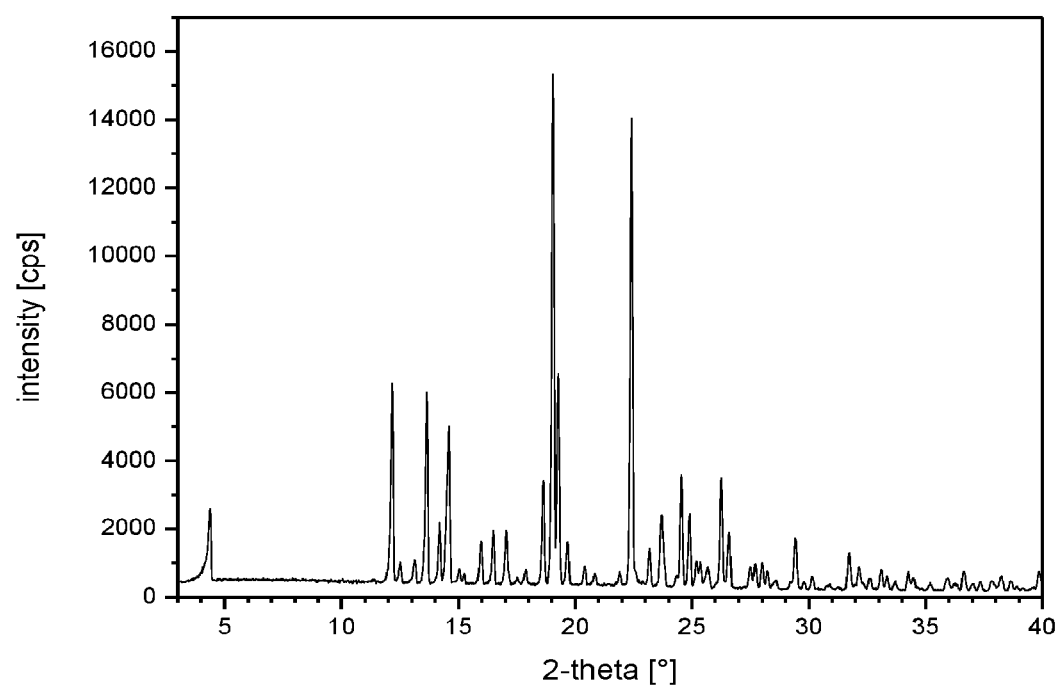
FIG. 2 shows the X-ray powder diffractogram of (4-((3R,4R)-3-methoxytetrahydro-pyran-4-yl)amino)piperidin-1-yl)(5-methyl-6-(((2R,6S)-6-(p-tolyl)tetrahydro-2H-pyran-2-yl)methylamino)pyrimidin-4-yl)methanone citrate.

In certain embodiments, the crystalline form has a X-ray powder diffraction pattern that is substantially as shown in FIG. 2.

In certain embodiments, the crystalline form is characterized by the following X-ray powder diffraction pattern expressed in terms of diffraction angle 2θ, inter-planar distances d, and relative intensity (expressed as a percentage with respect to the most intense peak):

| 2-theta [°] | d-value [Å] | Intensity $I/I_0$ [%] |
| --- | --- | --- |
| 4.36 | 20.24 | 17 |
| 12.17 | 7.27 | 41 |
| 12.51 | 7.07 | 6 |
| 13.13 | 6.74 | 7 |
| 13.66 | 6.48 | 39 |
| 14.20 | 6.23 | 14 |
| 14.60 | 6.06 | 32 |
| 15.03 | 5.89 | 5 |
| 15.25 | 5.81 | 4 |
| 15.97 | 5.54 | 11 |
| 16.51 | 5.37 | 13 |
| 17.05 | 5.20 | 13 |
| 17.54 | 5.05 | 4 |
| 17.88 | 4.96 | 5 |
| 18.65 | 4.75 | 22 |
| 19.05 | 4.66 | 100 |
| 19.68 | 4.51 | 11 |
| 20.42 | 4.35 | 6 |
| 20.84 | 4.26 | 4 |
| 21.25 | 4.18 | 3 |
| 21.90 | 4.06 | 5 |
| 22.42 | 3.96 | 92 |
| 23.19 | 3.83 | 9 |
| 23.70 | 3.75 | 16 |
| 24.34 | 3.65 | 4 |
| 24.56 | 3.62 | 23 |
| 24.89 | 3.57 | 16 |
| 25.20 | 3.53 | 7 |
| 25.36 | 3.51 | 7 |
| 25.67 | 3.47 | 6 |

-continued

| 2-theta [°] | d-value [Å] | Intensity I/I₀ [%] |
|---|---|---|
| 26.26 | 3.39 | 23 |
| 26.59 | 3.35 | 12 |
| 27.51 | 3.24 | 6 |
| 27.71 | 3.22 | 6 |
| 28.01 | 3.18 | 7 |
| 28.23 | 3.16 | 5 |
| 28.57 | 3.12 | 3 |
| 29.44 | 3.03 | 12 |
| 30.15 | 2.96 | 4 |

The crystalline form may be further characterized according to its Raman spectrum. Accordingly, in certain embodiments, the crystalline form has a Raman spectrum comprising peaks at any one or all of the following Raman shifts expressed in wavenumbers in cm⁻¹: 1718, 1242, 731, 662, 553.

The crystalline form may be further characterized according to its melting point. Accordingly, in certain embodiments, the crystalline form has a melting point of 212±5° C.

Figure 3:
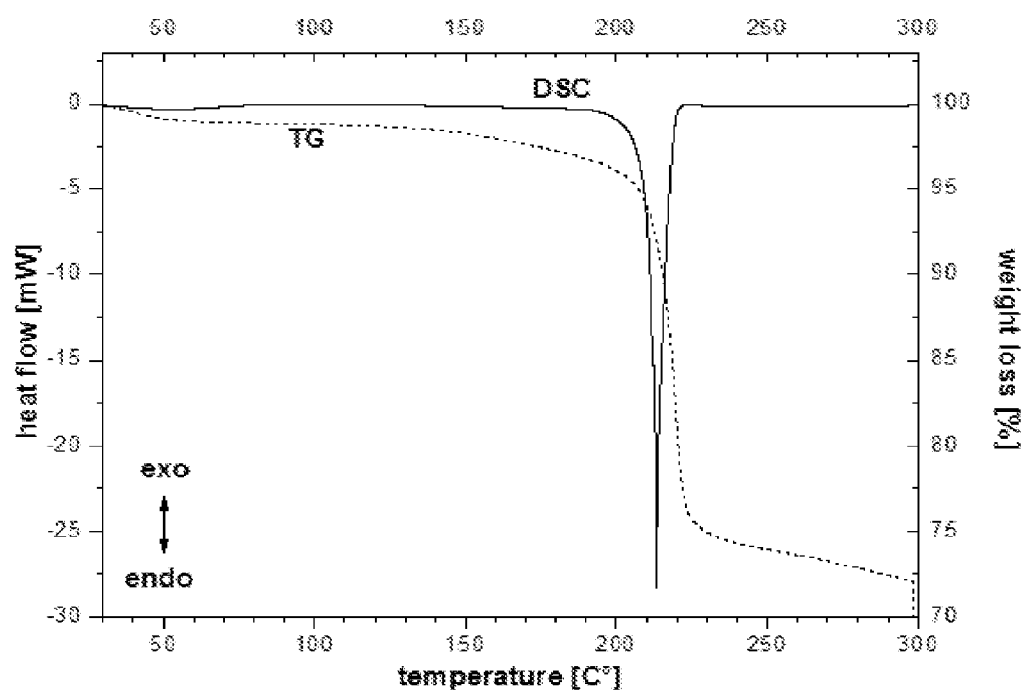
FIG. 3 shows the thermoanalysis and determination of the melting point (DSC/TG) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate.

The crystalline form may be further characterized according to its differential scanning calorimetry curve. Accordingly, in certain embodiments, the crystalline form has a differential scanning calorimetry curve substantially the same as shown in FIG. 3.

Desirably the molar ratio of citric acid to 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone is about 1:1 in a citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl) methanone. In certain embodiments, the molar ratio of citric acid to 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone is in the range of 1.2:1 to 1:1.2 in a citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone. In certain other embodiments, the molar ratio of citric acid to 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone is 1:1 in a citrate salt of 4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone.

The compound (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl) methanone (I) is specifically disclosed in WO 2011/073154, as well as a process for its preparation. For details on a process to manufacture this compound, reference is thus made to WO 2011/073154 (example 30, page 150).

Methods for preparing citrate salt 1 are also provided. For example, one aspect of the invention provides a method for preparing compound 1

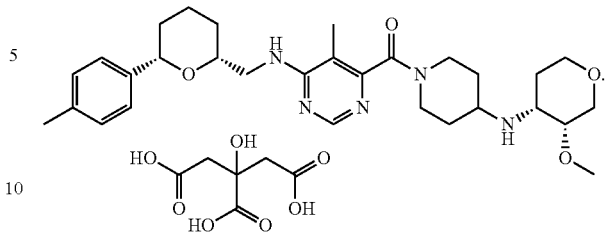

comprising the following steps:
a) addition of citric acid to a solution of compound I

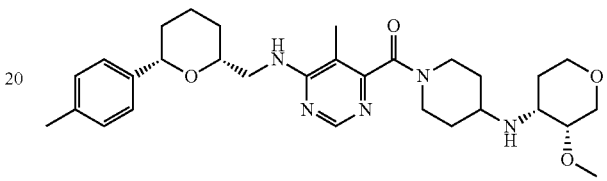

in an organic solvent
b) isolation of the resulting salt 1 in pure form.

In certain embodiments, the method is further characterized in that the organic solvent in step a) is selected from the group consisting of ethyl acetate, isopropanol and a mixture of isopropanol and water.

II. Therapeutic Applications

Compounds such as those described in Section I (e.g., citrate salt 1) and pharmaceutical compositions described herein are useful as a medicament. The medicament may be for treating a disorder in which inhibition of CCR2 activity provides a therapeutic benefit.

The Chemokine receptor CCR2 has been reported to be implicated as being an important mediator of inflammatory and immunoregulatory disorders and diseases as well as autoimmune pathologies such as rheumatoid arthritis and atherosclerosis. See, for example, WO 2010/070032. Thus, agents that modulate the chemokine receptor CCR2 are useful in treating such disorders and diseases.

More generally, it is widely accepted that numerous conditions and diseases involve inflammatory processes. Such inflammations are critically triggered and/or promoted by the activity of macrophages, which are formed by differentiation out of monocytes. It has further been found that monocytes are characterized by, e.g., a high expression of membrane-resident CCR2, whereas the CCR2 expression in macrophages is lower. CCR2 is a critical regulator of monocytes trafficking, which can be described as the movement of the monocytes towards an inflammation along a gradient of monocyte chemoattractant proteins (MCP-1, MCP-2, MCP-3, MCP-4).

Therefore, in order to reduce macrophage-induced inflammation, it would be desirable to block the monocyte CCR2 by an antagonist, so that the monocytes can be less triggered to move towards an inflammation area for conversion into macrophages.

Accordingly, one aspect of the invention provides a method of treating a CCR2-related condition in a patient, where the method comprises administering to a patient in need thereof a therapeutically effective amount of a compound described herein (e.g., the citrate salt 1 or a crystalline form thereof) to treat the condition. In certain embodiments, the CCR2-related condition is a MCP-1 related condition.

In certain embodiments, the CCR2-related condition is pain. Exemplary types of pain contemplated for treatment, include, for example, inflammatory pain, neuropathic pain, and visceral pain. In certain embodiments, the pain is chronic pain. In certain embodiments, the pain is pain due to osteoarthritis. Other exemplary types of pain contemplated for treatment include, for example, low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain.

In certain other embodiments, the CCR2-related condition is an immune related disease. Exemplary immune-related diseases include, for example, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, and ulcerative colitis.

In certain other embodiments, the CCR2-related condition is a fibrotic condition. Exemplary fibrotic conditions include, for example, liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; neurofibromatosis; fibroma; intestinal fibrosis; and fibrotic adhesions resulting from surgical procedures.

In certain other embodiments, the CCR2-related condition is an inflammatory disorder.

Another aspect of the invention provides a method of treating a condition selected from pain, osteoarthritis, diabetic nephropathy, and diabetic polyneuropathy, where the method comprises administering to a patient in need thereof a therapeutically effective amount of a compound described herein (e.g., the citrate salt 1 or a crystalline form thereof) to treat the condition.

In certain embodiments, the condition is pain. In certain embodiments, the condition is inflammatory pain. In certain embodiments, the condition is chronic pain. In certain embodiments, the condition is pain due to osteoarthritis. In certain embodiments, the condition is neuropathic pain or visceral pain.

In certain embodiments, the condition is selected from the group consisting of acute and chronic mild to moderate musculoskeletal pain, low back pain, chronic low back pain, pain related to rheumatoid arthritis, shoulder pain, dental pain, signs and symptoms of osteoarthritis, osteoarthritis of the knee, osteoarthritis of the hip, osteoarthritis of the hand, pain associated with osteoarthritis, cancer pain, diabetic polyneuropathy, visceral pain, acute pain, diabetic nephropathy, and neuropathic pain. In certain embodiments, the condition is pain selected from (a) trigeminal neuralgia and (b) pain due to chemotherapy caused nerve injury.

In certain embodiments, the condition is osteoarthritis.

In certain embodiments, the method comprises administering to the patient a therapeutically effective amount of citrate salt 1 to treat the condition.

In a more specific embodiment, the invention provides for using a compound described herein for the treatment of a disease in which inhibition of the CCR2 receptor is beneficial, such as: (i) acute and chronic mild to moderate musculoskeletal pain (low back pain, chronic low back pain, pain related to rheumatoid arthritis, shoulder pain, dental pain); (ii) signs and symptoms of osteoarthritis (osteoarthritis of the knee and/or hip, osteoarthritis of the hand, pain associated with osteoarthritis); (iii) cancer pain; (iv) diabetic polyneuropathy; (v) visceral pain, (vi) acute pain, (vii) diabetic nephropathy; and (viii) neuropathic pain.

III. Pharmaceutical Compositions

Another aspect of the invention provides a pharmaceutical composition comprising a compound described herein (e.g., citrate salt 1) together with one or more inert carriers and/or diluents. The pharmaceutical compositions may be formulated for administration via a particular route, such as oral administration.

More generally, suitable forms for administration are, for example, tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e., in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers. Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration, the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

IV. Kits for Use in Medical Applications

Another aspect of the invention provides a kit for treating a medical condition. The kit comprises: i) instructions for treating a medical condition, such as pain, osteroarthritis, diabetic nephropathy, or diabetic polyneuropathy (for example, pain such as selected from acute and chronic mild to moderate musculoskeletal pain, low back pain, chronic low back pain, pain related to rheumatoid arthritis, shoulder pain, dental pain, pain associated with osteoarthritis, cancer pain, visceral pain, acute pain, diabetic nephropathy, and neuropathic pain); and ii) a compound described herein, such as citrate salt 1. The kit may comprise one or more unit dosage forms containing an amount of citrate salt 1 that is effective for treating said medical condition, such as pain.

EXAMPLES

The invention now being generally described, will be more readily understood by reference to the following examples, which are included merely for purposes of illustration of certain aspects and embodiments of the present invention, and are not intended to limit the invention.

LIST OF ABBREVIATIONS

AUC area under the plasma concentration-time curve
BR hydrobromide (salt with hydrobromic acid)
BS base (no salt defined)
$C_{max}$ peak concentration
CI citrate (salt with citric acid)
CL clearance
CL hydrochloride (salt with hydrochloric acid)
ES esilate (salt with one mol ethanesulfonic acid)
d.b. (on) dry basis
DSC Differential Scanning calorimeter
DMSO dimethyl sulfoxide
DMSO-$d_6$ deuterated DMSO
DVS Dynamic vapour sorption
EDTA Ethylenediaminetetraacetic acid
EGTA ethylene glycol tetraacetic acid
ESI electrospray ionization
f female
F oral bioavailability
FCS fetal calf serum
HEPES 4-(2-hydroxyethyl)-1-piperazineethanesulfonic acid
hERG human ether-a-go-go-related gene
HR high-resolution
IV, i.v. intravenous
m male
M mol/L
McIlvaine buffer citrate/phosphate buffer
$MRT_{disp}$ mean residence time following intravenous dosing
$MRT_{tot}$ mean residence time following oral dosing
MS mass spectrometry
MS methanesulfonate (salt with one mol methanesulfonic acid)
m/z mass-to-charge ratio
NMR nuclear magnetic resonance
PBS phosphate buffered saline
PK pharmacokinetics
PO, p.o. peroral
r.h. relative humidity
RT room temperature
Sorensen buffer NaOH/NaCL/Glycin-buffer
$t_{max}$ time of maximum plasma concentration
TG ThermoGravimetry
$V_{ss}$ steady-state volume of distribution
VLE very low endotoxin
XRPD X-ray powder diffraction

Example 1—Preparation and Physicochemical Characterization of Salts of Compound I Multiple salts of compound I were prepared and characterized, including the citrate salt of compound I. Experimental procedures and results are provided below. Compound I has the following formula:

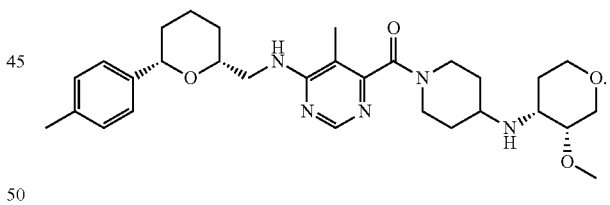

Part I: Description of Analytical Methods Used

Provided below is a description of analytical methods used to characterize salts of compound I.

ESI Mass Spectrometry (ESI+)

| | |
|---|---|
| Instrument | QTOF 2 (Micromass, Manchester, UK) |
| Instrument control software | Masslynx 4.1 |
| Ion source | ESI + (Lockspray source) |
| Lockspray/DXC | on/off |
| Calibration | 0.1% Phosphoric acid in acetonitrile/water (1:1), lockmass calibration |
| Resolution MS1(LM/HM) | 5/5 |

-continued

| | |
|---|---|
| Resolving power (FWHM) | 16000 at m/z 491 (W mode) |
| MCP voltage | 2200 V |
| Capillary voltage | +2.8 kV |
| Cone voltage | 25 V |
| Collision energy | 5 V |
| Collision gas | Argon |
| Source temperature | 120° C. |
| Desolvation temperature | 150° C. |
| Cone gas | nitrogen 75 L/h |
| Desolvation gas | nitrogen 450 L/h |
| Spray solvent | acetonitrile/water 9:1 |
| Syringe pump | Harvard Apparatus 55-2222 |
| Spray solvent flow rate | 5 μL/min |
| Sample concentration | 5 ng/μL spray solvent |
| Reagents | acetonitrile (ULC/MS, Biosolve) |
| | water (purified by Milli-Q-system) |
| Scan range | 50-1000 u (TOF scan, profile data) |
| Scan time | 2.9 s |
| No. of scans combined | 20 |
| Accurate mass determination | Center 5 points/80%, Np = 0.35, lockmass: 588.8692 |
| Data threshold | 1.0% |

$^1$H NMR Spectroscopy

| | |
|---|---|
| Instrument | Bruker DRX 400 |
| Frequency | 400.13 MHz |
| Software | TopSpin ® version 1.3 PL8 |
| Pulse program | zg30 |
| Solvent | DMSO-$d_6$ |
| Concentration | 10.3 mg/0.6 mL |
| Temperature | 30° C. |
| Calibration | TMS (δ = 0.00 ppm) |
| Sweep width | 8013 Hz |
| Size | 64K data points |
| Pulse width | 30 degree |
| Relaxation delay | 10 s |
| Number of scans | 32 |
| Dummy scans | 8 |
| Apodization | zerofilling to 128K data points |
| | Gaussian multiplication (GB: 0.25, LB: −0.25 Hz) |

$^{13}$C NMR Spectroscopy

| | |
|---|---|
| Instrument | Bruker DRX 400 |
| Frequency | 100.61 MHz |
| Software | TopSpin ® version 1.3 PL8 |
| Pulse program | Zgpg |
| Solvent | DMSO-$d_6$ |
| Concentration | 10.3 mg/0.6 ml |
| Temperature | 30° C. |
| Calibration | DMSO-$d_6$ (δ = 39.5 ppm) |
| Sweep width | 27778 Hz |
| Size | 64K data points |
| Pulse width | 90 degree |
| Relaxation delay | 4 s |
| Number of scans | 4096 |
| Dummy scans | 32 |
| Apodization | zerofilling to 128K data points |
| | Exponential multiplication (LB: 2.5 Hz) |

X-Ray Powder (XRPD) Diagram

X-ray powder diagrams were generated using a STOE-STADI P-diffractometer in transmission mode fitted with a MYTHEN-detector and a Cu-anode as X-ray source with monochromatic CuKα1 radiation (λ=1.54056 Å, 40 kV, 40 mA).

FT-RAMAN Spectroscopy

Samples have been measured in boiling point tubes using a Bruker RAM II FT-Raman Module instrument, resolution 2 cm$^{-1}$, 64 scans, laser power 500 mW (focussed laser). Analysis: scaling of vector in spectral range 3500 cm$^{-1}$-50 cm$^{-1}$.

Differential Scanning Calorimetry—Melting Point

The compounds are characterised by a melting point determined by Differential Scanning calorimetry (DSC), evaluated by the peak maximum or onset temperature. The heating rate of the experiment is 10° C./min. The values given were determined using a DSC instrument from the Q-Series™ of TA Instruments.

ThermoGravimetry (TG)

Thermal gravimetry data were collected with a TG instrument from the Q-series of TA Instruments. This method measures weight changes in a material as a function of temperature under a controlled atmosphere.

Dynamic Vapour Sorption (DVS)

Sorption isotherms were generated using an IGAsorp water sorption monitor from Hiden Isochema. Adsorption and desorption isotherms were obtained at 25° C. with 10% r.h. step intervals ranging from 10% r.h. to 90% r.h.

For BR salt form only: Sorption isotherms were registered on a DVS-1 water sorption monitor from Surface Measurement Systems.

Solubility

Solubility was determined using an automated shake flask method (at room temperature) and quantitation of the dissolved drug substance was determined by UV-spectroscopy within this automated setup.

Part II: Preparation of (4-((3R,4R)-3-Methoxytetra-hydro-pyran-4-ylamino)piperidin-1-yl)(5-methyl-6-(((2R,6S)-6-(p-tolyl)tetrahydro-2H-pyran-2-yl)meth-ylamino)pyrimidin-4-yl)methanone Citrate (1)

Exemplary procedures for making the title compound are provided below, along with physical characterization data. The preparation procedures include two different routes for making the title compound.

Preparation Option a) Preparation of Citrate Salt Starting from Free Base I

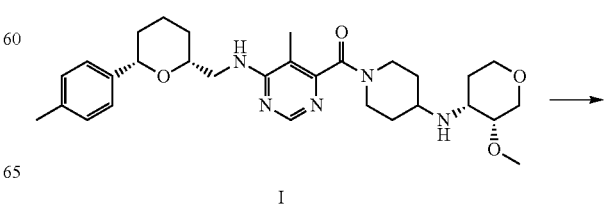

I

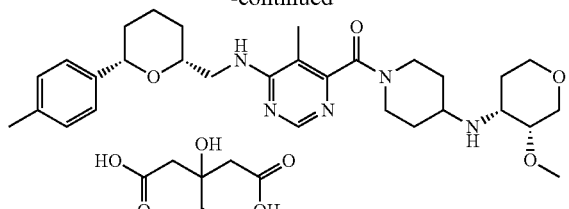

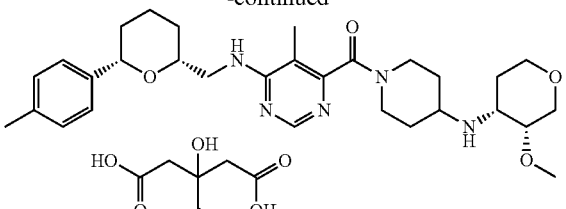

To a solution of the free base I (200 mg, 0.372 mmol) in ethyl acetate (2 mL) is added citric acid mono hydrate (78.2 mg; 0.372 mmol). The solution is stirred overnight (18 h). The suspension is filtered and the product is dried at 40° C. in vacuo to yield 140 mg 0.192 mmol (52%) colourless crystals. Physical characterization data for citrate salt 1 is provided below.

NMR ($^1$H, 400 MHz, DMSO-d$_6$): 11.7-8.5; (2H, broad), 8.34; (1H, s), 7.22; (2H, m), 7.12; (2H, m), 7.08; (1H, t), 4.49; (1H, m), 4.31; (1H, d), 4.09; (1H, m), 3.85; (1H, m), 3.74; (1H, m), 3.57-3.44; (2H, m), 3.48; (1H, m), 3.47; (1H, m), 3.35; (3H, s), 3.35; (1H, m), 3.33 (1H, m), 3.29; (1H, m), 3.27; (1H, m), 3.04; (1H, m), 2.84; (1H, m), 2.58; (2H, d), 2.50; (2H, d), 2.28; (3H, s), 2.12; (1H, m), 1.94; (1H, m), 1.91; (3H, s), 1.88; (1H, m), 1.78; (1H, m), 1.76 (1H, m), 1.70; (1H, m), 1.66; (1H, m), 1.63; (1H, m), 1.40; (1H, m), 1.40; (1H, m), 1.37; (1H, m), 1.24; (1H, m) (includes rotamers).

NMR ($^{13}$C, 100 MHz, DMSO-d$_6$): 176.6, 171, 165.4, 161.0, 156.6, 155.4, 140.3, 136.0, 128.5, 125.6, 109.3, 78.5, 75.4, 72.4, 72.2, 71.2, 64.8, 64.4, 64.4, 55.5, 55.5, 51.5, 51.4, 50.2, 45.6, 44.1, 44.1, 38.8, 33.3, 29.6, 28.7, 28.7, 25.1, 23.1, 20.6, 11.7 (includes rotamers).

HRMS (ESI): m/z 538.3400 ([M+H]$^+$; C$_{30}$H$_{44}$N$_5$O$_4$).

FT-RAMAN spectrum (characteristic bands) [cm$^{-1}$]: 1718, 1242, 731, 662, 553.

See table II below and FIGS. 2-4 and 17 for additional characterizing data.

Preparation Option b) Amide Coupling Followed by Preparation of Citrate Salt

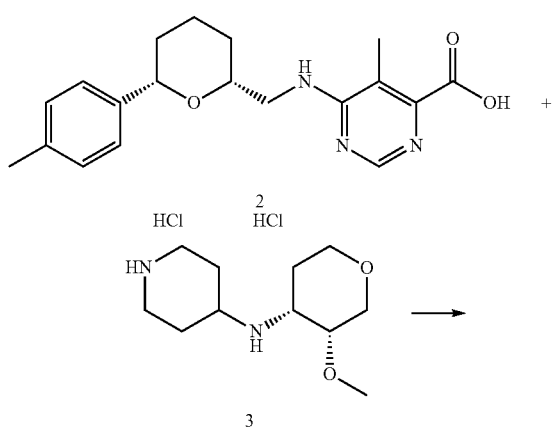

4.99 kg (30.75 mol) of 1,1'-carbonyldiimidazole are added to a suspension of 10.0 kg (29.29 mol) of 2 in 75 L of 2-methyltetrahydrofuran at 50° C. The powder funnel is rinsed with 5 L 2-methyltetrahydrofuran. The reaction mixture is stirred for 70 min at 50° C. Then, 8.83 kg (30.75 mol) of 3 are added to the reaction mixture and the funnel is rinsed with 5 L 2-methyltetrahydrofuran. Next, 7.41 kg (73.23 mol) of triethylamine and 10 L of 2-methyltetrahydrofuran are added and the reaction mixture is stirred for 1 h under reflux. Then, the mixture is cooled to 60° C. and a solution of 6.07 kg (43.94 mol) of potassium carbonate in 55 L water is added and the phases are separated at 55° C. The organic layer is washed with 60 L water and 80 L of solvent are removed by distillation in vacuo. The resulting residue is diluted with 80 L of isopropyl alcohol and 55 L of solvent is removed by distillation in vacuo. The resulting residue is diluted with 40 L of isopropyl alcohol and 40 L of solvent is removed by distillation in vacuo. Next, 5.85 kg (27.83 mol) of citric acid monohydrate in 11 L of water are added and the dropping funnel is rinsed with 30 L of isopropyl alcohol. The reaction mixture is heated to 75° C., stirred until a solution is formed, and then filtrated. The filter is rinsed with a mixture of 2 L of water and 20 L of isopropyl alcohol. Then, the filtrate is diluted with 30 L of isopropyl alcohol and seeded with 100 g of 1 as obtained in option a) at 65° C. Next, the mixture is cooled to 55° C. within 30 minutes and then further stirred for 1 h at 55° C. The resulting suspension is diluted with 60 L of isopropyl alcohol within 1 h at 55° C. and then cooled to 20° C. within 3 h. Then, the suspension is stirred for 17 h at 20° C. and isolated by filtration. The filter cake is washed twice with a mixture of 19 L of isopropyl alcohol and 1 L of water, each. The product is dried at 50° C. in vacuo to yield 17.76 kg of compound (83%). Physical characterization data for citrate salt 1 is provided below.

NMR ($^1$H, 400 MHz, DMSO-d$_6$): 11.7-8.5; (2H, broad), 8.34; (1H, s), 7.22; (2H, m), 7.12; (2H, m), 7.08; (1H, t), 4.49; (1H, m), 4.31; (1H, d), 4.09; (1H, m), 3.85; (1H, m), 3.74; (1H, m), 3.57-3.44; (2H, m), 3.48; (1H, m), 3.47; (1H, m), 3.35 (3H, s), 3.35; (1H, m), 3.33 (1H, m), 3.29; (1H, m), 3.27; (1H, m), 3.04; (1H, m), 2.84; (1H, m), 2.58; (2H, d), 2.50; (2H, d), 2.28; (3H, s), 2.12; (1H, m), 1.94; (1H, m), 1.91; (3H, s), 1.88; (1H, m), 1.78; (1H, m), 1.76; (1H, m), 1.70; (1H, m), 1.66 (1H, m), 1.63; (1H, m), 1.40; (1H, m), 1.40; (1H, m), 1.37; (1H, m), 1.24; (1H, m) (includes rotamers).

NMR ($^{13}$C, 100 MHz, DMSO-d$_6$): 176.6, 171, 165.4, 161.0, 156.6, 155.4, 140.3, 136.0, 128.5, 125.6, 109.3, 78.5, 75.4, 72.4, 72.2, 71.2, 64.8, 64.4, 64.4, 55.5, 55.5, 51.5, 51.4, 50.2, 45.6, 44.1, 44.1, 38.8, 33.3, 29.6, 28.7, 28.7, 25.1, 23.1, 20.6, 11.7 (includes rotamers).

HRMS (ESI): m/z 538.3400 ([M+H]$^+$; C$_{30}$H$_{44}$N$_5$O$_4$).

FT-RAMAN spectrum (characteristic bands) [cm$^{-1}$]: 1718, 1242, 731, 662, 553.

See table II below and FIGS. 2-4 and 17 for additional characterizing data.

Part III: Preparation of Additional Salts of (4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone Additional salts of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone were prepared and characterized as described below.

Preparation of (4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrobromide 1.916 mL (0.1 M) of hydrobromic acid is added to a solution of 103 mg (0.1916 mmol) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone in 2 mL of methanol and stirred for 2 h at 50° C. Then, the solvent is removed in a vacuum dryer at 40° C. Next, 4 mL of tetrahydrofuran is added to the residue. The mixture is sonicated, then stirred for 2 h at 40° C., and afterwards stored for 4 h at room temperature. Then, the solvent is removed in a vacuum dryer to yield the hydrobromide of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone.

See table III below and FIGS. 5-7 for characterizing data.

Preparation of (4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrochloride 0.558 mL (0.1 M) of hydrochloric acid is added to a solution of 30 mg (0.0557 mmol) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone in 1 mL of methanol and stirred for 2 h at 50° C. Then, the solvent is removed in a vacuum dryer at 40° C. Next, 1.2 mL of tetrahydrofuran is added to the residue. The mixture is sonicated, then stirred for 2 h at 40° C., and afterwards stored for 4 h at room temperature. Then, the solvent is removed in a vacuum dryer to yield the hydrochloride of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone.

See table IV below and FIGS. 8-10 for characterizing data.

Preparation of (4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone Esilate 1.860 mL (0.1 M) of ethanesulfonic acid is added to a solution of 100 mg (0.186 mmol) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone in 2 mL of methanol and stirred for 2 h at 50° C. Then, the solvent is removed in a vacuum dryer at 40° C. Next, 4 mL of acetone is added to the residue. The mixture is sonicated, then stirred for 2 h at 40° C., and afterwards stored for 4 h at room temperature. Then, the solvent is removed in a vacuum dryer to yield the esilate of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone.

FT-RAMAN spectrum (characteristic bands) [cm$^{-1}$]: 1637, 1253, 1014, 740, 719, 534, 525, 219.

See table V below and FIGS. 11-13 and 18 for characterizing data.

Preparation of (4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone methanesulfonate 0.558 mL (0.1 M) of methanesulfonic acid is added to a solution of 30 mg (0.0557 mmol) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone in 1 mL methanol and stirred for 2 h at 50° C. Then, the solvent is removed in a vacuum dryer at 40° C. Next, 1.2 mL toluene is added to the residue. The mixture is sonicated, then stirred for 2 h at 50° C., and afterwards stored over night at room temperature. Then, the solvent is removed in a vacuum dryer to yield the methanesulfonate of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone.

See table VI below and FIGS. 14-16 for characterizing data.

Part IV: Physical Characterization Data for Salts of (4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone Exemplary physical characterization data for salts of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone is provided below.

Solubility in Aqueous Media

Table I shows the solubility of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate in different aqueous media at 2, 4 and 6 h.

TABLE I

| Medium | 2 h [mg/ml] | 4 h [mg/ml] | 6 h [mg/ml] |
| --- | --- | --- | --- |
| Water | >1 | >1 | >1 |
| 0.1N HCl | >1 | >1 | >1 |
| 0.01N HCl | >1 | >1 | >1 |
| McIlvaine buffer pH 2.2 | >1 | >1 | >1 |
| McIlvaine buffer pH 3.0 | >1 | >1 | >1 |
| McIlvaine buffer pH 4.0 | >1 | >1 | >1 |
| McIlvaine buffer pH 4.5 | Not determined | >1 | >1 |

TABLE I-continued

| Medium | 2 h [mg/ml] | 4 h [mg/ml] | 6 h [mg/ml] |
|---|---|---|---|
| McIlvaine buffer pH 5.0 | >1 | >1 | >1 |
| McIlvaine buffer pH 6.0 | >1 | >1 | >1 |
| McIlvaine buffer pH 6.8 | >1 | >1 | >1 |
| McIlvaine buffer pH 7.4 | >1 | >1 | >1 |
| $KH_2PO_4$-buffer pH 7.4 | >1 | >1 | >1 |
| Sörensen pH 10 | >1 | >1 | >1 |
| 0.1N NaOH | >1 | >1 | >1 |
| EtOH | 9.2 | 9.8 | 10 |

The data in table I demonstrate that (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate is highly soluble in acidic, neutral and basic aqueous media.

Solid State Properties of Citrate Salt 1

Various solid state properties of citrate salt 1 are described below.

Appearance

In the solid state, (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate is a white microcrystalline material.

Sorption Behaviour

Only (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate shows stability against relative humidity up to 80%. An uptake of 2.6% water is observed. The water uptake is reversible, and after the sorption experiment the compound still remains as solid material. All other salts turned into liquid phase at higher relative humidity (depending on the salt form starting at 60-70% relative humidity).

Crystallinity and Polymorphism

Citrate Salt 1

Citrate salt 1 is highly crystalline as can be seen in the X-ray powder diffraction diagram in FIG. 2. The X-ray powder reflection and intensities (standardised) are shown in Table II.

TABLE II

| 2-theta [°] | d-value [Å] | Intensity $I/I_0$ [%] |
|---|---|---|
| 4.36 | 20.24 | 17 |
| 12.17 | 7.27 | 41 |
| 12.51 | 7.07 | 6 |
| 13.13 | 6.74 | 7 |
| 13.66 | 6.48 | 39 |
| 14.20 | 6.23 | 14 |
| 14.60 | 6.06 | 32 |
| 15.03 | 5.89 | 5 |
| 15.25 | 5.81 | 4 |
| 15.97 | 5.54 | 11 |
| 16.51 | 5.37 | 13 |
| 17.05 | 5.20 | 13 |
| 17.54 | 5.05 | 4 |
| 17.88 | 4.96 | 5 |
| 18.65 | 4.75 | 22 |
| 19.05 | 4.66 | 100 |
| 19.68 | 4.51 | 11 |
| 20.42 | 4.35 | 6 |
| 20.84 | 4.26 | 4 |
| 21.25 | 4.18 | 3 |
| 21.90 | 4.06 | 5 |
| 22.42 | 3.96 | 92 |
| 23.19 | 3.83 | 9 |
| 23.70 | 3.75 | 16 |
| 24.34 | 3.65 | 4 |
| 24.56 | 3.62 | 23 |
| 24.89 | 3.57 | 16 |
| 25.20 | 3.53 | 7 |
| 25.36 | 3.51 | 7 |
| 25.67 | 3.47 | 6 |
| 26.26 | 3.39 | 23 |
| 26.59 | 3.35 | 12 |
| 27.51 | 3.24 | 6 |
| 27.71 | 3.22 | 6 |
| 28.01 | 3.18 | 7 |
| 28.23 | 3.16 | 5 |
| 28.57 | 3.12 | 3 |
| 29.44 | 3.03 | 12 |
| 30.15 | 2.96 | 4 |

In Table II above, the value "2-theta [°]" denotes the angle of diffraction in degrees and the d-value [Å] denotes the specified distances in Å between the lattice planes.

The crystalline citrate salt of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone is characterised in that the x-ray powder diagram has, inter alia, the characteristic values 2-theta=19.1° (100% relative intensity), 22.4° (92% relative intensity), 12.2° (41% relative intensity), 13.7° (39% relative intensity), and 14.6° (32% relative intensity) (which are the most prominent peaks in the diagram of FIG. 2, Table II).

Therefore, according to a first aspect, the invention provides a citrate salt of compound I

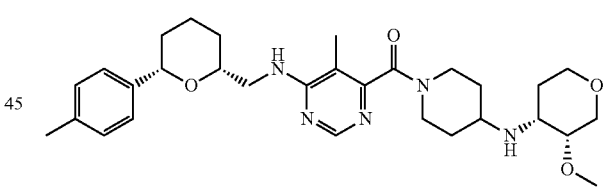

having the formula

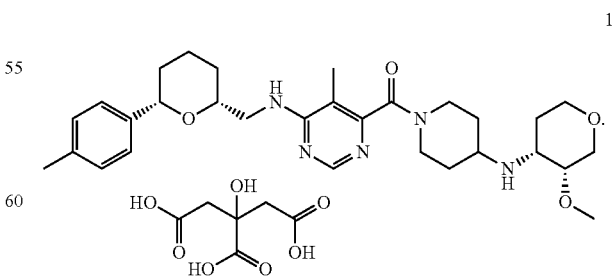

In a second embodiment, salt 1 is in crystalline form.
In a third embodiment, according to any one of the preceding embodiments, the crystalline form of compound 1 shows a X-ray powder diffraction pattern comprising peaks at the following 2-theta values measured using monochromatic CuKα1 radiation of λ=1.54056 Å, 40 kV, 40 mA: 19.1° and 22.4°.

In a further embodiment according to any one of the preceding embodiments, the crystalline form shows a X-ray powder diffraction pattern further comprising a peak at 12.2°.

In a further embodiment according to any one of the preceding embodiments, the crystalline form shows a X-ray powder diffraction pattern further comprising a peak at 13.7°.

In a further embodiment according to any one of the preceding embodiments, the crystalline form shows a X-ray powder diffraction pattern further comprising a peak at 14.6°.

In a further embodiment according to any one of the preceding embodiments, the crystalline form shows a X-ray powder diffraction pattern further comprising a peak at 18.7°.

In a further embodiment according to any one of the preceding embodiments, the crystalline form shows a X-ray powder diffraction pattern further comprising a peak at 24.6°.

In a further embodiment according to any one of the preceding embodiments, the crystalline form shows a X-ray powder diffraction pattern further comprising a peak at 26.3°.

In a further embodiment according to any one of the preceding embodiments, the crystalline form shows a Raman spectrum comprising peaks at any one or all of the following Raman shifts expressed in wavenumbers in cm$^{-1}$: 1718, 1242, 731, 662, 553.

In a further embodiment according to any one of the preceding embodiments, the crystalline form shows a melting point of 212±5° C.

The citrate salt 1 may be provided in a pharmaceutical composition. Accordingly, another aspect of the present invention is a pharmaceutical composition containing the salt according to any one of the preceding embodiments optionally together with one or more inert carriers and/or diluents.

Only one crystalline form has been obtained from several experiments for (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate.

Hydrobromide Salt of Compound of Formula (I)

Figure 5:
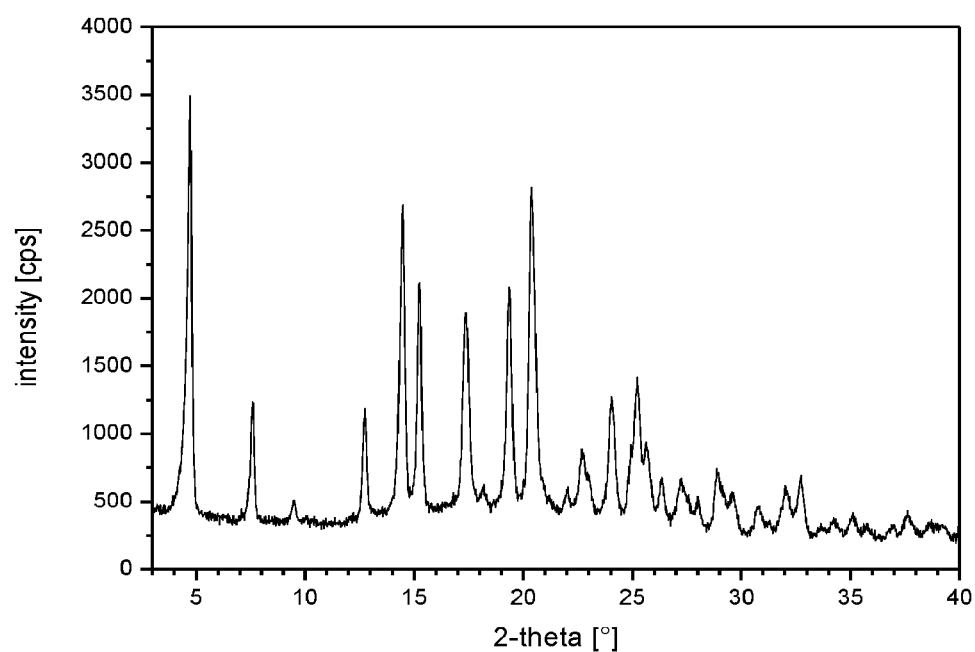
FIG. 5 shows the X-ray powder diffractogram of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrobromide.
Figure 6:
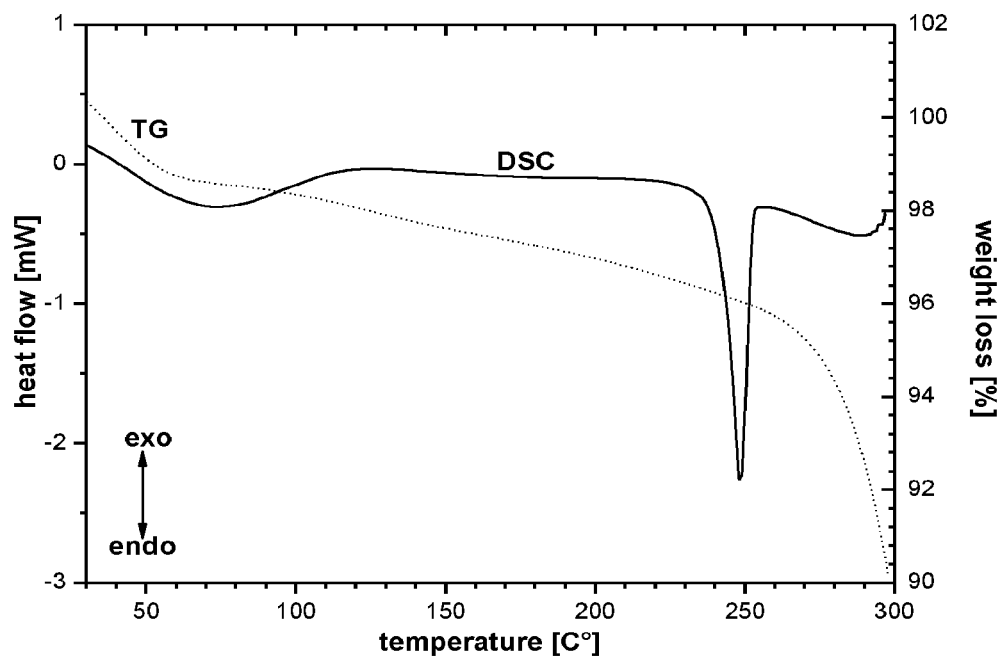
FIG. 6 shows the thermoanalysis and determination of the melting point (DSC/TG) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrobromide.

The hydrobromide salt of compound of formula (I) is of medium crystallinity as demonstrated in the X-ray powder diffraction diagram in FIG. 5. The X-ray powder reflection and intensities (standardised) are shown in Table III.

TABLE III

| 2-theta [°] | d-value [Å] | Intensity I/I$_0$ [%] |
| --- | --- | --- |
| 4.73 | 18.67 | 100 |
| 7.60 | 11.62 | 37 |
| 9.48 | 9.32 | 15 |
| 12.74 | 6.94 | 34 |
| 14.46 | 6.12 | 78 |
| 15.25 | 5.81 | 62 |
| 17.38 | 5.10 | 56 |
| 18.16 | 4.88 | 17 |
| 19.36 | 4.58 | 62 |

TABLE III-continued

| 2-theta [°] | d-value [Å] | Intensity I/I$_0$ [%] |
| --- | --- | --- |
| 20.39 | 4.35 | 83 |
| 22.01 | 4.03 | 17 |
| 22.72 | 3.91 | 25 |
| 24.05 | 3.70 | 37 |
| 24.94 | 3.57 | 26 |
| 25.23 | 3.53 | 41 |
| 25.65 | 3.47 | 27 |
| 26.35 | 3.38 | 19 |
| 27.25 | 3.27 | 19 |
| 28.00 | 3.18 | 15 |
| 28.92 | 3.08 | 21 |
| 29.49 | 3.02 | 15 |
| 29.59 | 3.02 | 16 |

In Table III above, the value "2-theta [°]" denotes the angle of diffraction in degrees and the d-value [Å] denotes the specified distances in Å between the lattice planes.

(4-(3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrobromide is characterised in that the x-ray powder diagram has, inter alia, the characteristic values 2-theta=4.7° (100% relative intensity), 20.4° (83% relative intensity), 14.5° (78% relative intensity), 15.3° (62% relative intensity), and 19.4° (62% relative intensity) (which are the most prominent peaks in the diagram of FIG. 5, Table III).

Different polymorphic modifications of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrobromide have been identified by X-ray powder diffraction.

Hydrochloride Salt of Compound of Formula (I)

Figure 8:
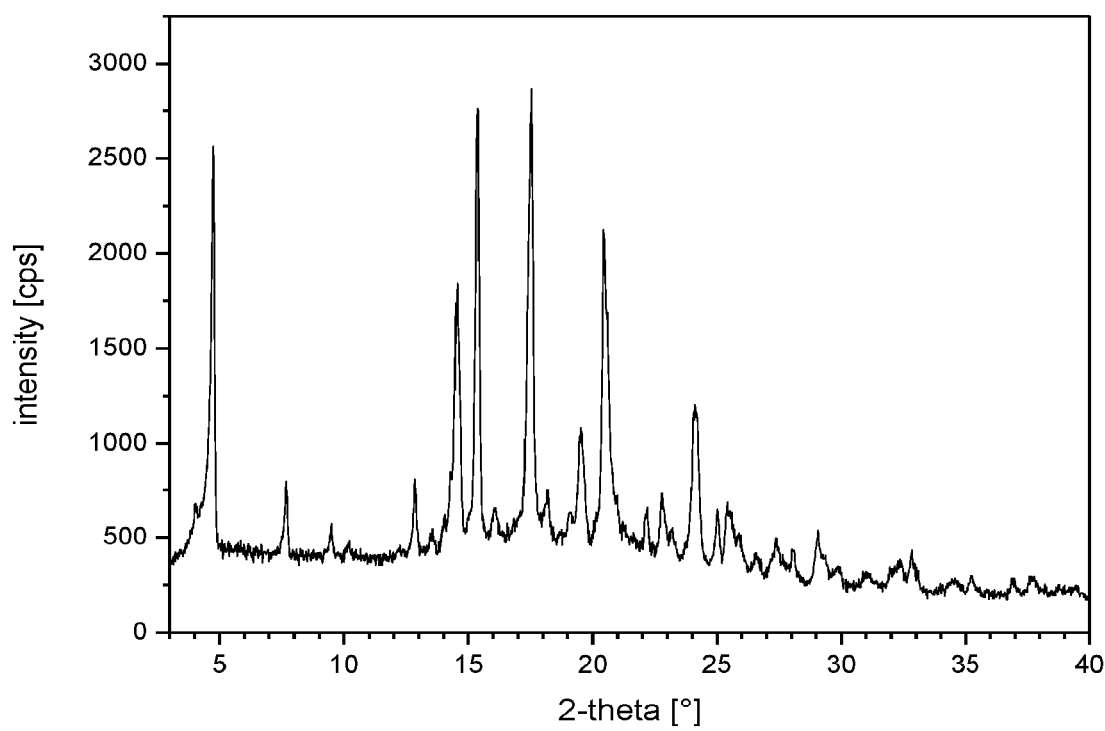
FIG. 8 shows the X-ray powder diffractogram of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrochloride.
Figure 9:
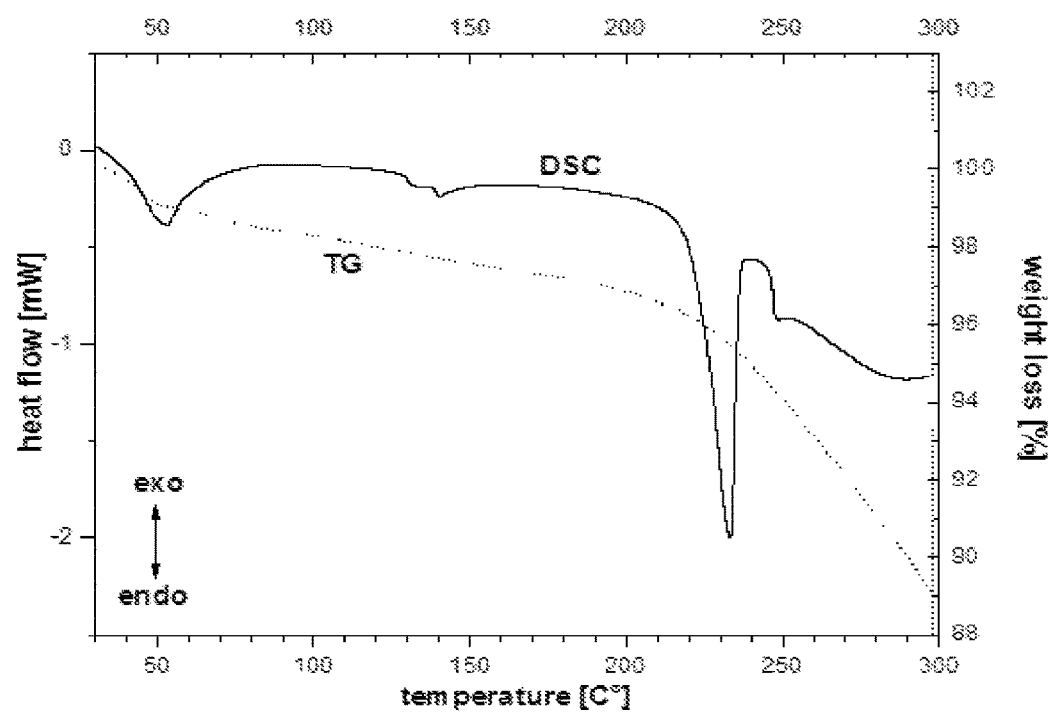
FIG. 9 shows the thermoanalysis and determination of the melting point (DSC/TG) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrochloride.

The hydrochloride salt of compound of formula (I) is of medium crystallinity as can be seen in the X-ray powder diffraction diagram in FIG. 8. The X-ray powder reflection and intensities (standardised) are shown in Table IV.

TABLE IV

| 2-theta [°] | d-value [Å] | Intensity I/I$_0$ [%] |
| --- | --- | --- |
| 4.05 | 21.78 | 24 |
| 4.74 | 18.63 | 93 |
| 7.68 | 11.50 | 28 |
| 9.49 | 9.31 | 19 |
| 10.17 | 8.69 | 17 |
| 12.27 | 7.21 | 16 |
| 12.85 | 6.88 | 29 |
| 13.55 | 6.53 | 19 |
| 14.05 | 6.30 | 22 |
| 14.55 | 6.08 | 64 |
| 15.37 | 5.76 | 98 |
| 16.09 | 5.51 | 23 |
| 16.58 | 5.34 | 19 |
| 17.52 | 5.06 | 100 |
| 18.14 | 4.89 | 25 |
| 19.12 | 4.64 | 23 |
| 19.53 | 4.54 | 39 |
| 20.46 | 4.34 | 77 |
| 22.16 | 4.01 | 23 |
| 22.79 | 3.90 | 26 |
| 23.22 | 3.83 | 20 |
| 24.13 | 3.69 | 44 |
| 25.02 | 3.56 | 23 |
| 25.42 | 3.50 | 24 |
| 25.87 | 3.44 | 18 |
| 26.57 | 3.35 | 15 |
| 27.39 | 3.25 | 18 |
| 28.06 | 3.18 | 16 |

TABLE IV-continued

| 2-theta [°] | d-value [Å] | Intensity I/I₀ [%] |
|---|---|---|
| 29.07 | 3.07 | 18 |
| 29.85 | 3.00 | 12 |

In Table IV above, the value "2-theta [° ]" denotes the angle of diffraction in degrees and the d-value [Å] denotes the specified distances in Å between the lattice planes.

(4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrochloride is characterised in that the x-ray powder diagram has, inter alia, the characteristic values 2-theta=17.5° (100% relative intensity), 15.4 (98% relative intensity), 4.7° (93% relative intensity), 20.5° (77% relative intensity), and 14.6° (64% relative intensity), (which are the most prominent peaks in the diagram of FIG. 8, Table IV).

Different polymorphic modifications of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrochloride have been identified by X-ray powder diffraction.

Esilate Salt of Compound of Formula (I)

Figure 11:
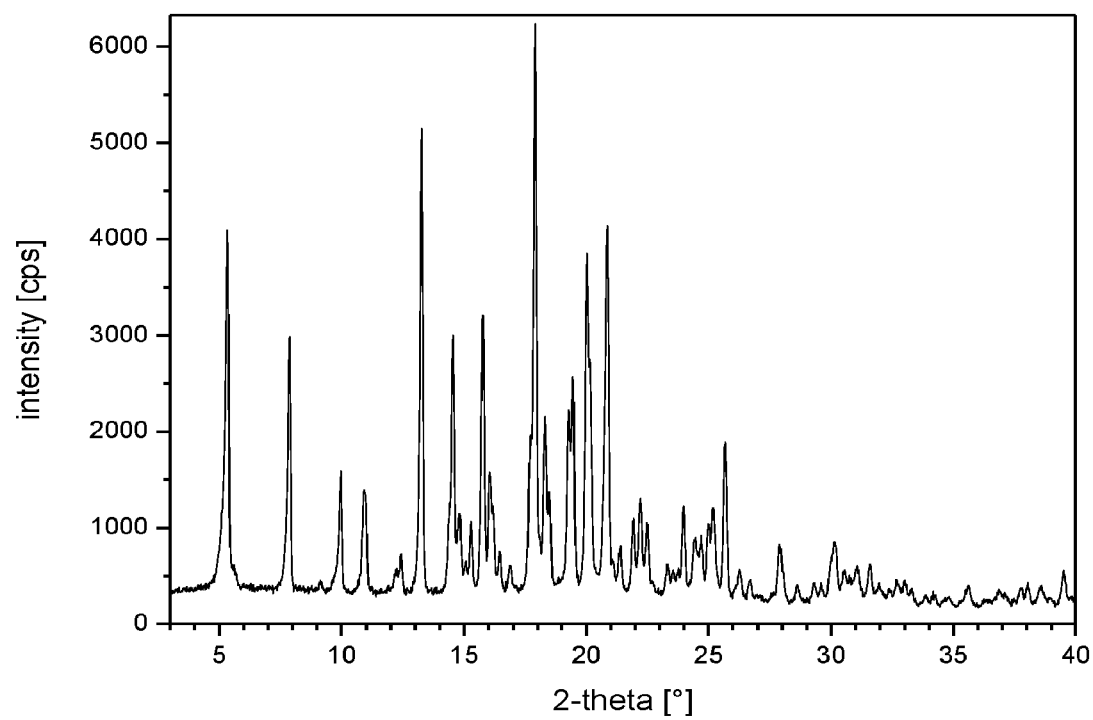
FIG. 11 shows the X-ray powder diffractogram of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone esilate.

The esilate salt of compound of formula (I) is of high crystallinity as can be seen in the X-ray powder diffraction diagram in FIG. 11. The X-ray powder reflection and intensities (standardised) are shown in Table V.

TABLE V

| 2-theta [°] | d-value [Å] | Intensity I/I₀ [%] |
|---|---|---|
| 5.33 | 16.56 | 66 |
| 7.87 | 11.23 | 48 |
| 9.14 | 9.67 | 7 |
| 9.97 | 8.87 | 24 |
| 10.93 | 8.09 | 23 |
| 12.23 | 7.23 | 9 |
| 12.43 | 7.12 | 11 |
| 13.26 | 6.67 | 83 |
| 14.55 | 6.08 | 48 |
| 14.83 | 5.97 | 18 |
| 15.07 | 5.88 | 10 |
| 15.29 | 5.79 | 17 |
| 15.77 | 5.61 | 51 |
| 16.05 | 5.52 | 25 |
| 16.18 | 5.47 | 19 |
| 16.46 | 5.38 | 12 |
| 16.88 | 5.25 | 10 |
| 17.90 | 4.95 | 100 |
| 18.32 | 4.84 | 34 |
| 18.49 | 4.79 | 22 |
| 19.29 | 4.60 | 36 |
| 19.44 | 4.56 | 40 |
| 20.03 | 4.43 | 63 |
| 20.14 | 4.41 | 45 |
| 20.85 | 4.26 | 66 |
| 21.08 | 4.21 | 11 |
| 21.37 | 4.15 | 12 |
| 21.92 | 4.05 | 18 |
| 22.22 | 4.00 | 21 |
| 22.49 | 3.95 | 16 |
| 22.71 | 3.91 | 7 |
| 23.33 | 3.81 | 10 |
| 23.53 | 3.78 | 9 |
| 23.79 | 3.73 | 8 |
| 23.98 | 3.71 | 20 |
| 24.43 | 3.64 | 15 |
| 24.68 | 3.60 | 14 |
| 25.00 | 3.56 | 17 |

In Table V above, the value "2-theta [°]" denotes the angle of diffraction in degrees and the d-value [Å] denotes the specified distances in Å between the lattice planes.

(4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone esilate is characterised in that the x-ray powder diagram has, inter alia, the characteristic values 2-theta=17.9° (100% relative intensity), 13.3 (83% relative intensity), 5.3° (66% relative intensity), 20.9° (66% relative intensity), and 20.0° (63% relative intensity) (which are the most prominent peaks in the diagram of FIG. 11, Table V).

Methanesulfonate Salt of Compound of Formula (I)

Figure 14:
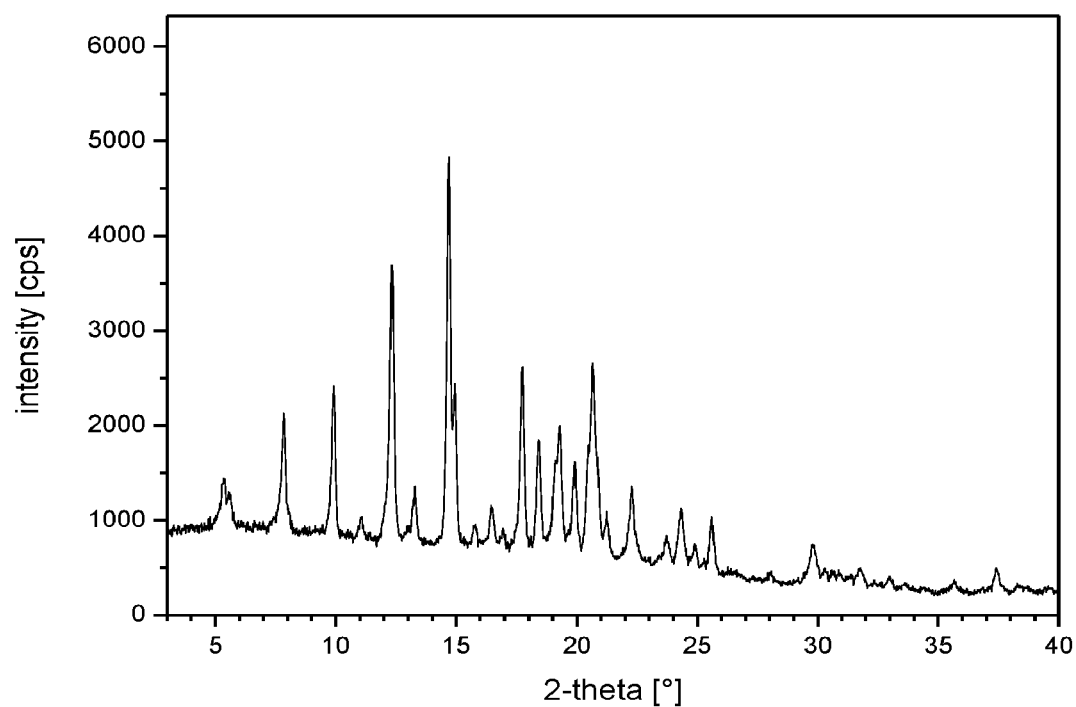
FIG. 14 shows the X-ray powder diffractogram of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone methanesulfonate.
Figure 15:
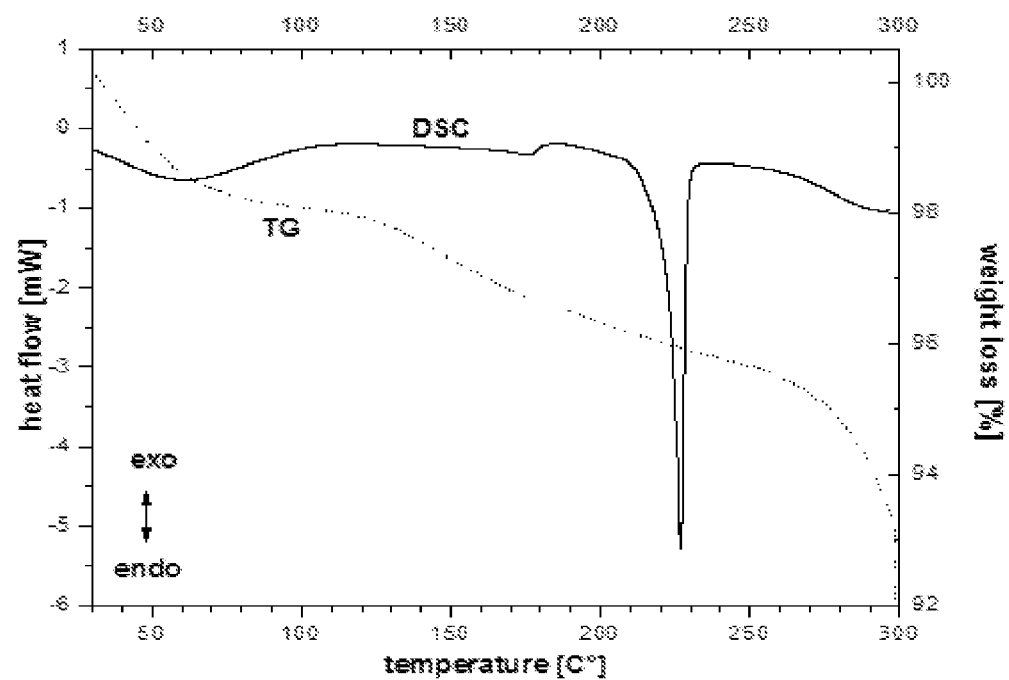
FIG. 15 shows the thermoanalysis and determination of the melting point (DSC/TG) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone methanesulfonate.

The methanesulfonate salt of compound of formula (I) is of medium crystallinity as can be seen in the X-ray powder diffraction diagram in FIG. 14. The X-ray powder reflection and intensities (standardised) are shown in Table VI.

TABLE VI

| 2-theta [°] | d-value [Å] | Intensity I/I₀ [%] |
|---|---|---|
| 5.36 | 16.48 | 30 |
| 5.57 | 15.85 | 27 |
| 7.84 | 11.27 | 43 |
| 9.91 | 8.92 | 51 |
| 11.05 | 8.00 | 21 |
| 12.33 | 7.17 | 77 |
| 13.26 | 6.67 | 26 |
| 14.69 | 6.03 | 100 |
| 14.95 | 5.92 | 50 |
| 15.78 | 5.61 | 20 |
| 16.47 | 5.38 | 23 |
| 17.74 | 4.99 | 53 |
| 18.42 | 4.81 | 38 |
| 19.09 | 4.65 | 33 |
| 19.29 | 4.60 | 41 |
| 19.91 | 4.46 | 32 |
| 20.67 | 4.29 | 55 |
| 21.23 | 4.18 | 21 |
| 22.28 | 3.99 | 28 |
| 23.74 | 3.74 | 16 |
| 24.33 | 3.66 | 23 |
| 24.84 | 3.58 | 15 |
| 25.60 | 3.48 | 21 |
| 29.79 | 3.00 | 16 |
| 17.74 | 16.48 | 30 |
| 18.42 | 15.85 | 27 |
| 19.09 | 11.27 | 43 |

In Table VI above, the value "2-theta [°]" denotes the angle of diffraction in degrees and the d-value [Å] denotes the specified distances in Å between the lattice planes.

(4-((3R,4R)-3-Methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone methanesulfonate is characterised in that the x-ray powder diagram has, inter alia, the characteristic values 2-theta=14.7° (100% relative intensity), 12.3 (77% relative intensity), 20.7° (55% relative intensity), 17.7° (53% relative intensity), and 9.9° (51% relative intensity) (which are the most prominent peaks in the diagram of FIG. 14, Table VI).

Thermoanalysis

The thermoanalysis of the crystalline citrate salt 1 shows a melting point=212±5° C. (onset, DSC: 10 K·min$^{-1}$ heating rate; DSC/TG diagram is shown in FIG. 3). 1.6% weight loss occurs on drying. Consequently, the citrate salt has a low tendency to absorb solvents (in case of water meaning low hygroscopicity).

The thermoanalysis of the crystalline hydrobromide salt of compound I shows a melting point=248±5° C. (onset, DSC: 10 K·min$^{-1}$ heating rate; DSC/TG diagram is shown in FIG. 6). A broad endothermic effect occurs between 40-110° C. with concomitant weight loss (2.9% weight loss on drying).

The thermoanalysis of the crystalline hydrochloride salt of compound I shows a melting point=233±5° C. (onset, DSC: 10 K·min$^{-1}$ heating rate; DSC/TG diagram is shown in FIG. 9). A broad endothermic effect occurs between 40-80° C. A weak endothermic effect occurs between 130-150° C. (2.8% weight loss on drying).

Figure 12:
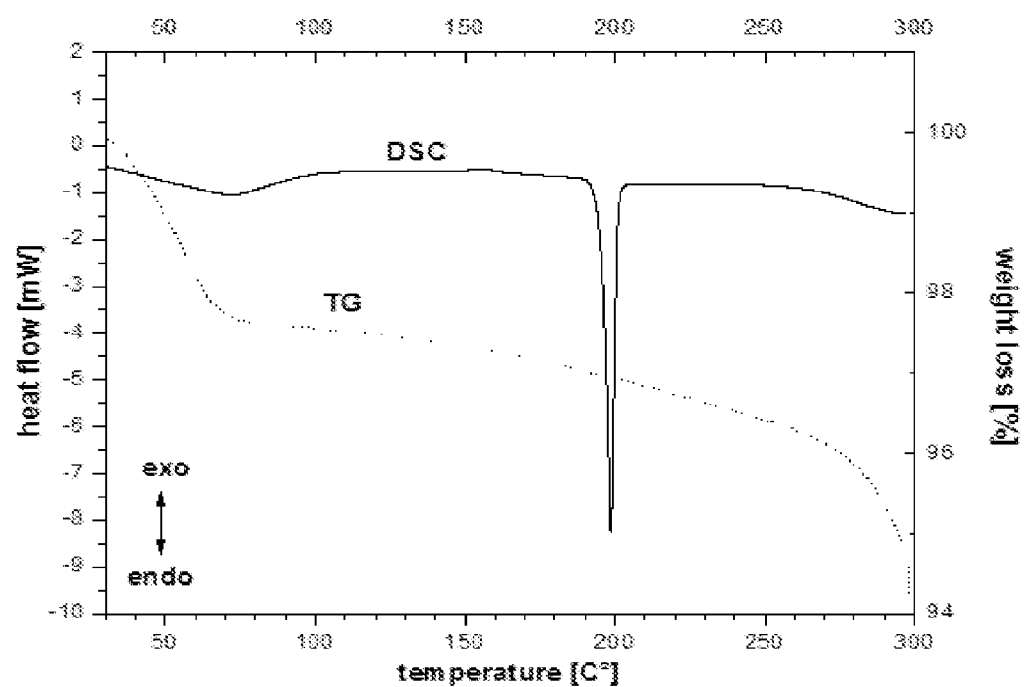
FIG. 12 shows the thermoanalysis and determination of the melting point (DSC/TG) of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone esilate.

The thermoanalysis of the crystalline esilate salt of compound I shows a melting point=199±5° C. (onset, DSC: 10 K·min$^{-1}$ heating rate; DSC/TG diagram is shown in FIG. 12). A weak broad endothermic effect occurs between 40-100° C. 2.4% loss on drying is correlated with the endothermic effect.

The thermoanalysis of the crystalline methanesulfonate salt of compound I shows a melting point=226±5° C. (onset, DSC: 10 K·min$^{-1}$ heating rate; DSC/TG diagram is shown in FIG. 15). A weak broad endothermic effect occurs between 30-110° C.

Sorption Isotherms

Figure 4:
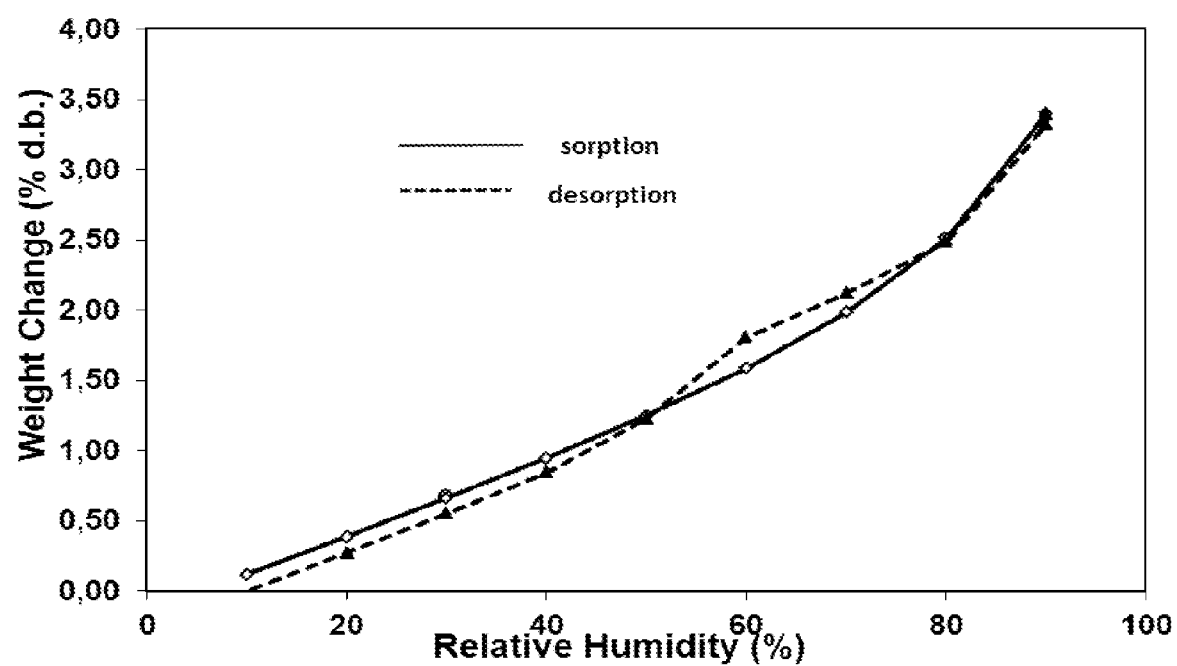
FIG. 4 shows the sorption isotherms of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone citrate.

The Sorption isotherm of the crystalline citrate salt 1 shows a water uptake of 2.6% in the humidity range of 10-80% (diagram shown in FIG. 4).

Figure 7:
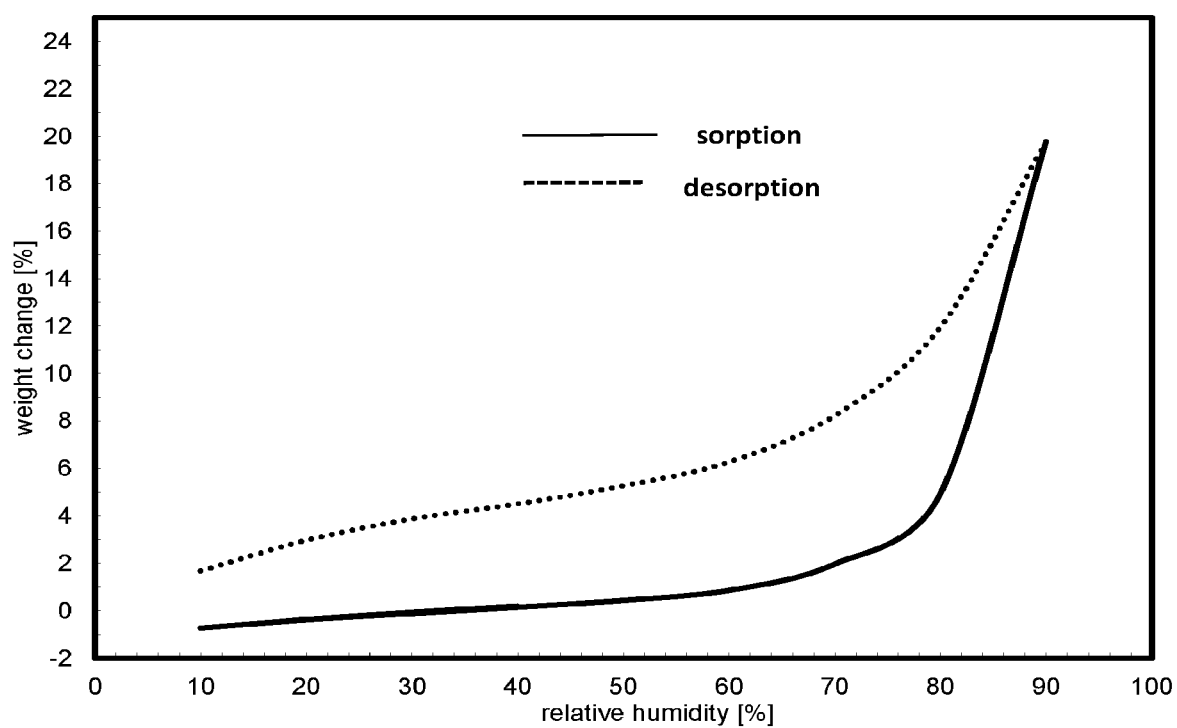
FIG. 7 shows the sorption isotherms of (4-((3R,4R)-3-methoxytetrahydro-pyran-4-ylamino)piperidin-1-yl)(5-methyl-6-(((2R,6S)-6-(p-tolyl)tetrahydro-2H- pyran-2-yl)methylamino)pyrimidin-4-yl)methanone hydrobromide.

The Sorption isotherm of the crystalline hydrobromide salt of compound I shows a water uptake of 4.5% in the humidity range of 10-80% (diagram shown in FIG. 7).

Figure 10:
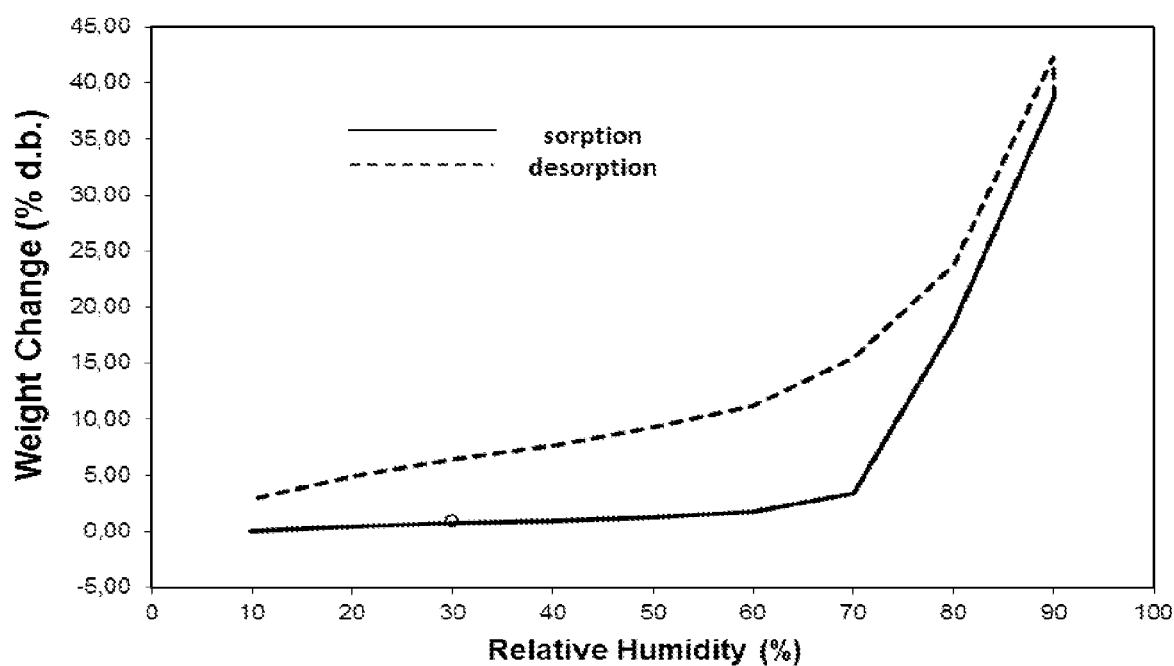
FIG. 10 shows the sorption isotherms of (4-((3R,4R)-3-methoxytetrahydro-pyran-4-ylamino)piperidin-1-yl)(5-methyl-6-(((2R,6S)-6-(p-tolyl)tetrahydro-2H-pyran-2-yl)methylamino)pyrimidin-4-yl)methanone hydrochloride.

The Sorption isotherm of the crystalline hydrochloride salt of compound I shows a water uptake of 15% in the humidity range of 10-80% (diagram shown in FIG. 10).

Figure 13:
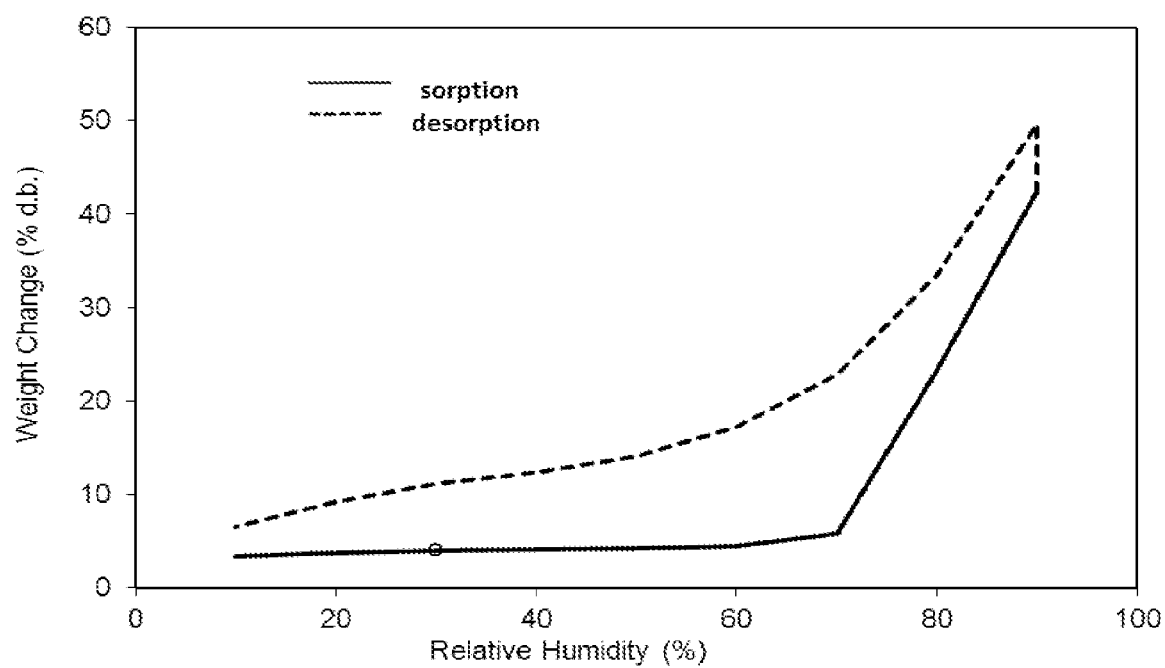
FIG. 13 shows the sorption isotherms of (4-((3R,4R)-3-methoxytetrahydro-pyran-4-ylamino)piperidin-1-yl)(5-methyl-6-(((2R,6S)-6-(p-tolyl)tetrahydro-2H- pyran-2-yl)methylamino)pyrimidin-4-yl)methanone esilate.

The Sorption isotherm of the crystalline esilate salt of compound I shows a water uptake of 20% in the humidity range of 10-80% (diagram shown in FIG. 13).

Figure 16:
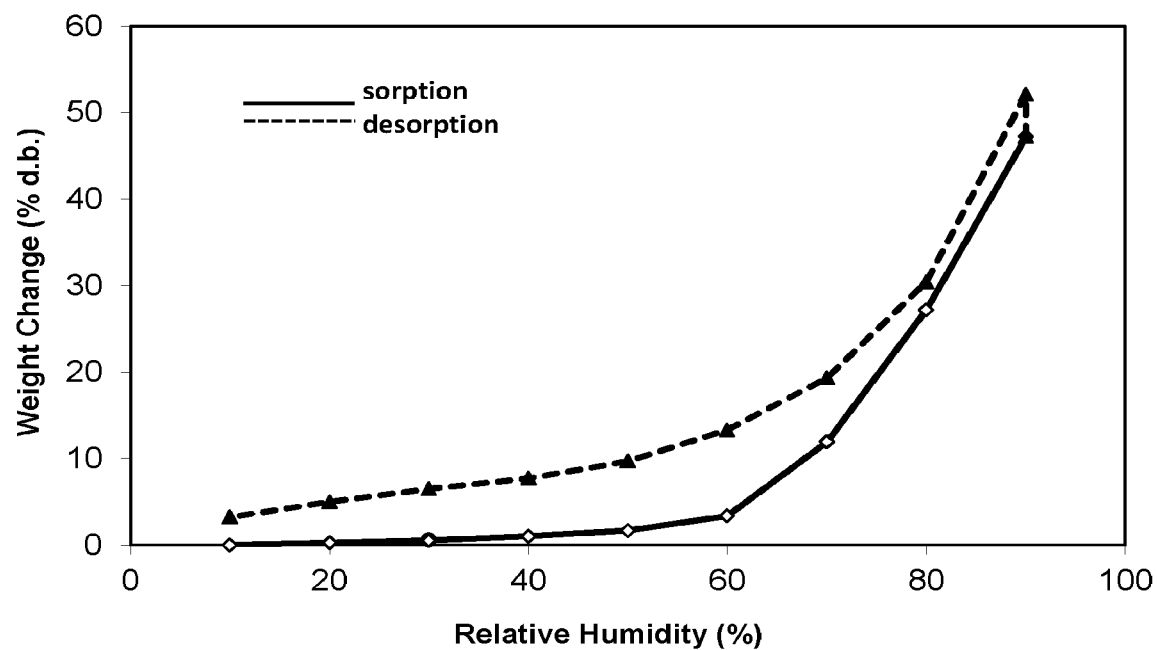
FIG. 16 shows the sorption isotherms of (4-((3R,4R)-3-methoxytetrahydro-pyran-4-ylamino)piperidin-1-yl)(5-methyl-6-(((2R,6S)-6-(p-tolyl)tetrahydro-2H- pyran-2-yl)methylamino)pyrimidin-4-yl)methanone methanesulfonate.
Figure 17:
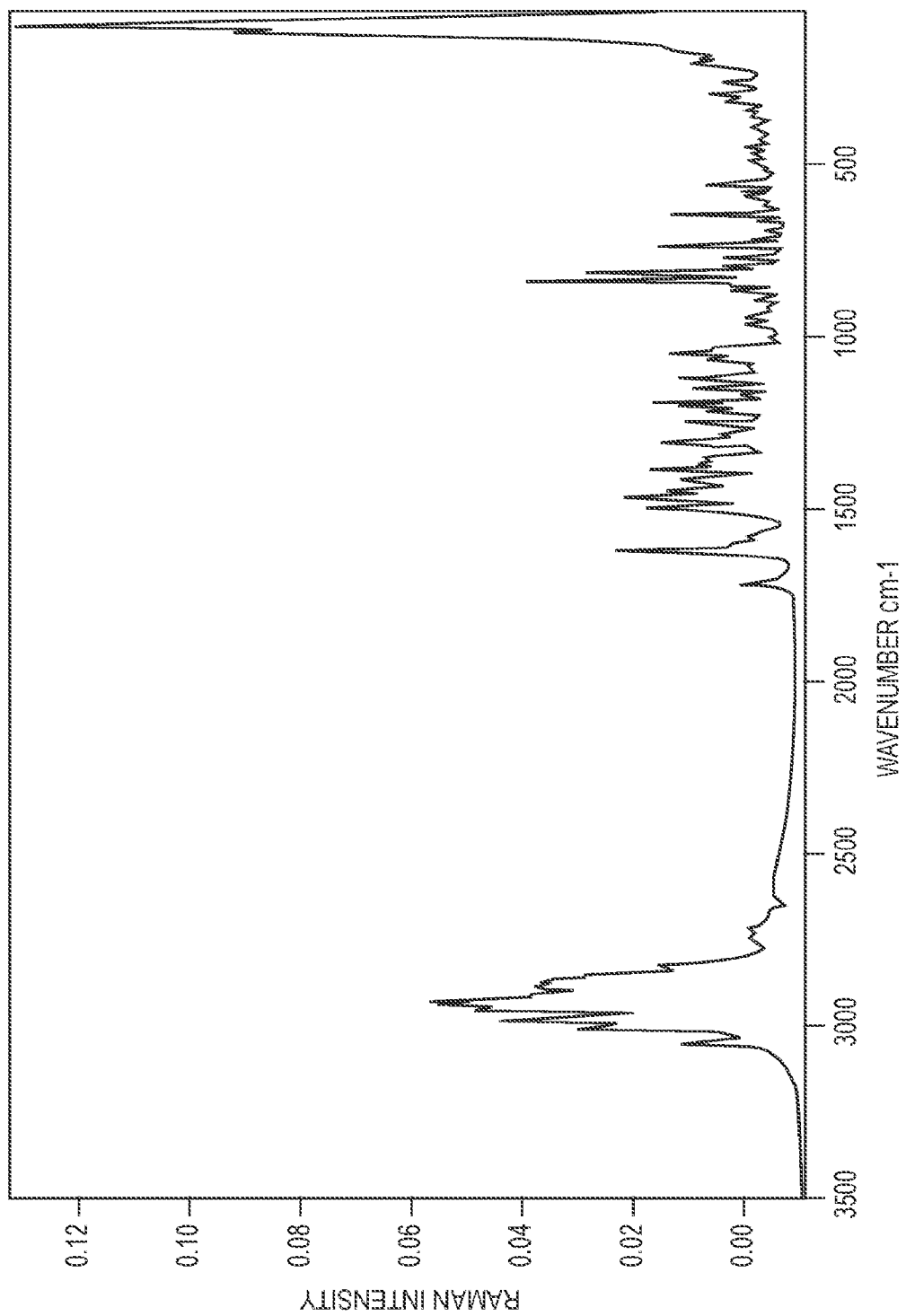
FIG. 17 shows the FT-RAMAN spectrum of (4-((3R,4R)-3-methoxytetrahydro-pyran-4-ylamino)piperidin-1-yl)(5-methyl-6-(((2R,6S)-6-(p-tolyl)tetrahydro-2H- pyran-2-yl)methylamino)pyrimidin-4-yl)methanone citrate.
Figure 18:
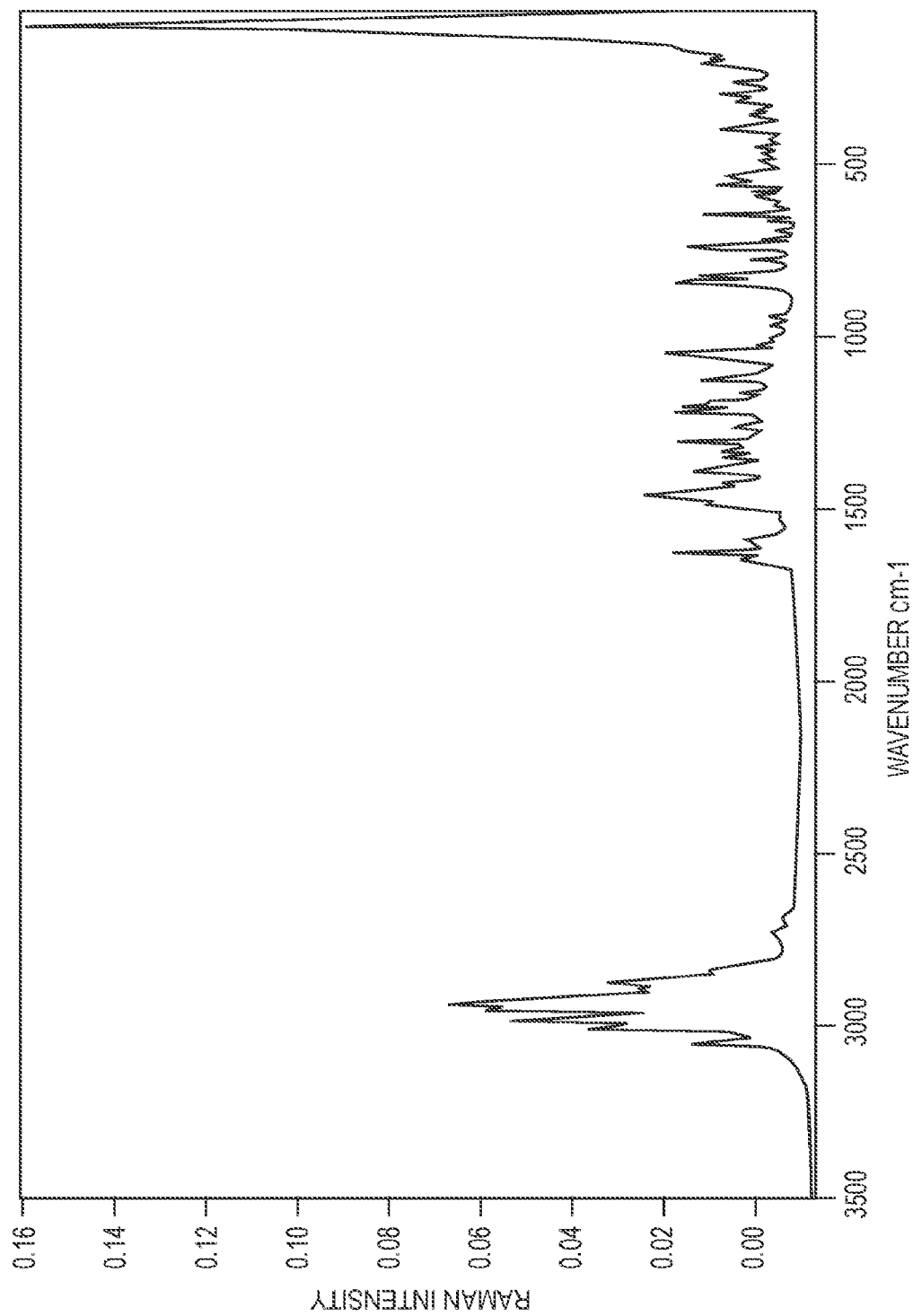
FIG. 18 shows the FT-RAMAN spectrum of (4-((3R,4R)-3-methoxytetrahydro-pyran-4-ylamino)piperidin-1-yl)(5-methyl-6-(((2R,6S)-6-(p-tolyl)tetrahydro-2H- pyran-2-yl)methylamino)pyrimidin-4-yl)methanone esilate.

The Sorption isotherm of the crystalline methanesulfonate salt of compound I shows a water uptake of 30% in the humidity range of 10-80% (diagram shown in FIG. 16).

Summary of Selected Physical Properties for Salts of Compound I

Selected properties of the citrate, hydrobromide, hydrochloride, esilate and methanesulfonate salts of compound I are shown in Table VII.

TABLE VII

| | Salt Form of Compound I | | | | |
|---|---|---|---|---|---|
| Parameter | Citrate salt | Hydrobromide Salt | Hydrochloride Salt | Esilate Salt | Methanesulfonate Salt |
| crystallinity | high | medium | medium | high | Medium |
| melting point [° C.] (onset) | 212 ± 5 | 248 ± 5 | 233 ± 5 | 199 ± 5 | 226 ± 5 |
| thermal behavior | no additional effect before melting | broad endothermic effect 40-110° C. | broad endothermic effect 40-80° C. weak endothermic effect 130-150° C. | weak broad endothermic effect 40-100° C. | weak broad endothermic effect 30-110° C. |
| loss on drying [%] | 1.6 | 2.9 | 2.8 | 2.4 | |
| hygroscopic behavior (up to 80% r.h.) | 2.6% uptake of water | 4.5% uptake of water deliquescent | 15% uptake of water deliquescent | 20% uptake of water deliquescent | 30% uptake of water |
| hygroscopic behavior (up to 90% r.h.) | 3.4% uptake of water | 20% uptake of water deliquescent | 40% uptake of water deliquescent | 45% uptake of water deliquescent | 45% uptake of water |
| indications for polymorphism | no | Yes | yes | no | No |

Example 2—Biological Activity Data Characterizing Compound I and its Citrate Salt 1

Experiments were performed to evaluate the biological activity of compound I and its citrate salt 1. A description of the experimental procedures and results are provided below.

Part I: Description of Biological Assays

Plasma Protein Binding

Dianorm Teflon dialysis cells (micro 0.2) are used. Each cell consists of a donor (i.e., buffer chamber) and an acceptor chamber (i.e., plasma chamber), separated by an ultrathin semipermeable membrane with a 5 kDa molecular weight cutoff. Stock solutions for each test compound are prepared in DMSO at 1 mM and diluted to a final concentration of 1.0 µM. Aliquots of 200 µl dialysis buffer (100 mM potassium phosphate, pH 7.4) are dispensed into the buffer chamber. Aliquots of 200 µL test compound dialysis solution are dispensed into the plasma chambers. Incubation is carried out for 2 hours under rotation at 37° C. Then, the dialysate is transferred into reaction tubes. The tubes for the buffer fraction contain 0.2 mL acetonitril/water (80/20 volume/volume). Aliquots of 25 µL of the plasma dialysate are transferred into deep well plates and mixed with 25 µL acetonitril/water (80/20 volume/volume), 25 µL buffer, 25

μL calibration solution and 25 μL Internal Standard solution. Protein precipitation is done by adding 200 μL acetonitrile. Aliquots of 50 μL of the buffer dialysate are transferred into deep well plates and mixed with 25 μL blank plasma, 25 μL Internal Standard solution and 200 μL acetonitril. Percent bound is calculated with the formula: % bound=(plasma concentration−buffer concentration/plasma concentration)×100.

In Vitro Metabolic Stability

Metabolic degradation of the test compound is assayed in a hepatocyte suspension. Hepatocytes are incubated in an appropriate buffer system. Following a (typically) 30 min preincubation in an incubator (37° C., 10% $CO_2$) 5 μL of test compound solution (1 μM) are added into 395 μL hepatocyte suspension (cell density in the range 0.25-5 Mio cells/mL, typically 1 Mio cells/mL, final DMSO concentration 0.05%). The cells are incubated for six hours (incubator, orbital shaker) and samples (25 μL) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended. Decline of parent compound is analyzed by HPLC-MS/MS. CLint is calculated as follows CL_INTRINSIC=Dose/AUC=(C0/CD)/(AUD+clast/k)×1000/60. C0: initial concentration in the incubation [μM], CD: cell density of vital cells [10e6 cells/mL], AUD: area under the data [μM×h], clast: concentration of last data point [μM], k: slope of the regression line for parent decline [h−1]. The calculated in vitro hepatic intrinsic clearance can be scaled up to the intrinsic in vivo hepatic Clearance and used to predict hepatic in vivo blood clearance (CL) by the use of a liver model (well stirred model).

CL_INTRINSIC_INVIVO [ml/min/kg]=(CL_INTRINSIC [μL/min/10e6 cells]×hepatocellularity [10e6 cells/g liver]×liver factor [g/kg bodyweight])/1000

CL [ml/min/kg]=CL_INTRINSIC_INVIVO [ml/min/kg]×hepatic blood flow [ml/min/kg]/(CL_INTRINSIC_INVIVO [ml/min/kg]+hepatic blood flow [ml/min/kg])

Pharmacokinetics (Animal Experiments)

The pharmacokinetics of the test compound following single intravenous (IV) or oral (PO) doses were examined in
female BALB/c mice (average weight: 25 g)
male Wistar(Han) rats (average weight: 260 g)
male and female Göttingen Minipigs (average weight: 24 kg)
male beagle dogs (average weight: 15 kg)
All non-rodent species were fasted overnight prior to dosing, while mice and rats had food and water available ad libitum. The p.o. dose of the compound was usually administered as suspension in 0.5% Natrosol or as a 0.5% Natrosol/0.015% Tween 80 suspension. For i.v. dosing purposes, the doses were applied as a solution in 0.9% NaCL, or as a solution containing 9.1% HP-beta Cyclodextrin in water.

Blood was collected by venous sampling and soaking of the blood in EDTA coated tubes. Samples were collected for up to 48 h after administration of the test compound. Plasma was then separated by centrifugation (5 min by approximately 9000 g at 4° C.). For determination of the test compound, plasma was transferred into PCR plates. All samples were stored at approximately −20° C. until bioanalytics. The test compound concentrations in plasma were determined by HPLC MS/MS. The lower limit of quantification was between 0.5 nmol/L and 1 nmol/L.

hERG-Channel Assay

Cells

HEK (human embryonic kidney) 293 cells were stably transfected with hERG cDNA. Cells determined for use in patch clamp experiments were cultivated without antibiotic.

Pipettes and Solutions

Cells were superfused with a bath solution containing (mM): NaCl (137), KCl (4.0), $MgCl_2$ (1.0), $CaCl_2$ (1.8), Glucose (10), HEPES (10), pH 7.4 with NaOH. Patch pipettes were made from borosilicate glass tubing (Hilgenberg, Malsfeld, Germany) using a horizontal puller (DMZ-Universal Puller, Zeitz-Instrumente, Martinsried, Germany) and filled with pipette solution containing (mM): K-aspartate (130), $MgCl_2$ (5.0), EGTA (5.0), $K_2ATP$ (4.0), HEPES (10.0), pH 7.2 with KOH. Resistance of the microelectrodes was in the range between 2 and 5 MΩ.

Stimulation and Recording

Membrane currents were recorded using an EPC-10 patch clamp amplifier (HEKA Electronics, Lambrecht, Germany) and PatchMaster software (HEKA). The current signals were Bessel filtered at 2.5 kHz before being digitized at 5 kHz.

hERG-mediated membrane currents were recorded at typically 28° C., using the whole-cell configuration of the patch-clamp technique. Transfected HEK293 cells were clamped at a holding potential of −60 mV and hERG-mediated inactivating tail currents were elicited using a pulse pattern with fixed amplitudes (activation/inactivation: 40 mV for 2000 ms; recovery: 120 mV for 2 ms; ramp to 40 mV in 2 ms; inactivating tail current: 40 mV for 50 ms) repeated at 15 s intervals. During each inter-pulse interval 4 pulses scaled down by a factor of 0.2 were recorded for a P/n leak subtraction procedure. $R_s$ compensation was employed up to a level that safely allowed recording devoid of ringing. The remaining uncompensated $R_s$ was recorded as well as actual temperature and holding current.

Compound Preparation and Application

The concentrations of the test item were applied sequentially on each of the different cells investigated. A steady state level of baseline current was measured for at least 90 s prior to the application of the first test article concentration.

The test item was dissolved in DMSO to yield a stock solution of 1000-fold the highest final concentration. This stock was diluted further in DMSO to stock solutions of 1000-fold the remaining final concentrations. Final dilutions in extracellular buffer were prepared freshly from these stocks by a 1:1000 dilution step each before starting the experiments.

Data Analysis

Peak current amplitudes were measured 3 ms after the ramp to +40 mV. For baseline and each concentration the peak currents of the three last sweeps before application of the next concentration were averaged. Residual currents ($I/I_0$) were calculated for each cell as the fraction of actual average peak current and average baseline peak current. Current inhibition was expressed as $(1-I/I_0)*100\%$. Current inhibition for all cells is reported as mean±SD. From mean current inhibition data, the $IC_{50}$ is estimated based on the Hill equation using a least squares procedure.

In Vitro Phospholipidosis Assay

1. Cell Culture

Cell line: U937. Cell density: 0.5 Mio. cells/mL. Amount of medium: 3 mL/well.

2. Materials and Devices

Falcon Tissue Culture Flask 175 $cm^2$
test tubes Sarstedt
6-well microplates
laminar flow
refrigerated centrifuge
pipettes
Flow cytometer: Coulter Epics XL/MCL (Beckman Coulter Inc., Bullerton, Calif., USA)

3. Medium and Additives 3.1 Preparation of RPMI1640 with 10% FCS and 0.005% Gentamicin Media VLE RPMI 1640 medium (1×), store at 2-8° C.

Additives fetal bovine serum, store at −20° C.
Gentamicin, Gibco® Invitrogen, conc. 10 mg/mL (=1% solution)
Add 56 mL FCS and 2.6 mL Gentamicin to 500 mL RPMI1640. Store the ready-to-use medium at 2-8° C.

3.2 Preparation of Formaldehyde Working Solution (conc. 3.7%)

Dilute Formaldehyde 37% in 1×PBS (dilution ratio 1:10) to make a 3.7% working solution, which is stored at 2-8° C.

3.3 Buffer

PBS-Dulbecco (1×) w/o $Ca^{2+}$, $Mg^{2+}$. Store at RT.

4. Dyes for Cell Staining 4.1 Live Cell Staining 4.1.1 Propidium Iodide (PI; Molecular Probes, Eugene, Oreg., USA)

PI stock solution: 1 mg/mL PBS (stored at 4° C. in the dark).
PI ready to use solution: stock solution 1:100 diluted with PBS (freshly prepared for each experiment).

4.1.2 Nile Red (NR; Molecular Probes, Eugene, Oreg.)

NR stock solution: 1 mg/mL DMSO (stored at 4° C. in the dark).
NR ready to use solution for live cell staining: NR stock solution 1:100 diluted with PBS (freshly prepared for each experiment).

4.2 Fixed Cell Staining

Preparation of Nile Red stock solution (conc. 1 mg/mL): solve 1 mg Nile Red in 1 mL 100% DMSO, store at 2-8° C.
Preparation of Nile Red working solution for fixed cell staining (conc. 1 µg/mL): dilute Nile Red stock solution in 1×PBS (dilution ratio 1:1000). The working solution must be prepared and used immediately before staining the cells.

5. Cell Seeding and Treatment

Cell seeding and treatment may be performed as follows:
solve the test compounds in 100% DMSO to the 100 fold final concentration and dilute them according to the experiment planned.
firstly fill 30 µL of the stock solution in the relevant well of the 6 well plate and re-suspend with
3 mL cell suspension/well containing 0.5 Mio. cells/mL (final concentration DMSO=1%).
use one well per compound and concentration
incubate 48 hours without changing the medium at 37° C., 5% $CO_2$ and 95% relative humidity 6. Cell Harvesting Cell harvesting may be performed as follows:
transfer the cell suspension in Sarstedt tubes (on ice)
centrifugation: 4 min at 130×g, 4° C.; discard the supernatant
re-suspend in 3 mL PBS per tube (ice cold)
fill 1 mL of the cell suspension in a Sarstedt tube (on ice) for flow cytometric determination (0.5 mL for Propidium-iodide and 0.5 mL for Nile Red live cell staining)
centrifugation of the residual: 4 min. at 130×g, 4° C.; discard the supernatant
add 1 mL 3.7% Formaldehyde solution per tube
fixation for 30 minutes (cells after fixation at RT)
centrifugation: 4 min at 130×g, RT; discard the supernatant
re-suspend each tube in 1.3 mL Nile Red working solution for fixed cell staining
incubate dye for 5 min
centrifugation: 4 min at 130×g, RT; discard the supernatant
re-suspend in 3 mL PBS
centrifugation: 4 min at 130×g, RT; discard the supernatant
re-suspend in 0.5 mL PBS (=fraction of Nile Red stained fixed cells), determination of phospholipidosis using a flow cytometric method 7. Cell Staining and Flow Cytometric Measurement 3×0.5 mL suspensions of cells are prepared from each sample for flow cytometry measurement (non-fixed cells for viability determination, non-fixed cells and fixed cells for phospholipidosis analysis).

7.1 PI Staining and Flow Cytometric Measurement for Viability Determination

Immediately before measurement, 12.5 µL of the PI ready to use solution is added per sample (0.5 mL non-fixed cell suspension), which are kept on ice for another 15 min before measurement.

Per sample, ten-thousand (10 000) cells are analyzed at high flow rate for the following parameter:

time to measure 10,000 cells, ungated forward scatter (linear) versus sideward scatter (linear), ungated yellow fluorescence ($\lambda$=568-590 nm; logarithmic) versus cell number (linear), ungated.

The time to measure 10,000 cells correlates to cell density in the sample.

Cut-off gates for the fluorescence-dependent differentiation between life and dead cells are defined based on the analysis of cell culture medium plus vehicle exposed Control cells. Cells with a fluorescence lower than the cut-off are defined as viable. Absolute viability of a sample is the relation of viable cells to total cell number and expressed as percentage.

7.2 Nile Red Staining and Flow Cytometric Measurement for PL Determination

7.2.1 Nile Red Live Cell Staining

Immediately before measurement, 50 μL of the NR ready to use solution for live cell staining is added per sample (0.5 mL non-fixed cell suspension). Samples are kept on ice for another 5 min. Thereafter, they are washed once with 4 mL PBS (4° C., 250×G for 8 min) and finally resuspended in 400 μL PBS.

7.2.2 Nile Red Fixed Cell Staining

Description see above (6. Cell harvesting). Both the Nile Red stained non-fixed cells as well as the Nile Red stained fixed cells are measured according the following procedure.

Per sample, 10,000 cells are analyzed at high flow rate for the following parameter:

forward scatter (linear) versus sideward scatter (linear), ungated green fluorescence ($\lambda$=504-541 nm; logarithmic) versus cell number (linear), ungated far red fluorescence ($\lambda$=660-680 nm; logarithmic) versus cell number (linear), ungated

8. Signal Analysis

Samples of less than 90% relative viability are excluded from analysis of the phospholipidogenic potential of a test compound. Samples with a viability between 90 to 95% are selected for assessment case by case depending on the consistency of all analyzed parameters and the absolute fluorescence intensity.

For all samples with a viability relative to Control of >90% (based on PI exclusion), the mean absolute fluorescence intensity following NR staining is calculated for green fluorescence as well as for far red fluorescence.

For each channel, absolute fluorescence intensity of a specific sample is correlated to the mean absolute fluorescence intensity of all cell culture medium plus vehicle exposed Control cells of the respective experiment. Per channel, relative fluorescence intensity of a sample is the relation of absolute fluorescence intensity of this sample to the mean absolute fluorescence intensity of Controls, which is set at 100, and is expressed as percentage of Control cell fluorescence intensity.

9. Assessment of Phopholipidosis

Assessment of the phospholipidogenic potential of a test compound is done manually based on the signal intensities at both wavelengths for the fixed cells as well as for the non-fixed cells.

Part II: Results of Biological Activity Assays for Compound I (Free Base) and its Citrate Salt 1

Tables below summarize biological data on compound I and its citrate salt 1, as determined in the assays as described above.

In Vitro Plasma Protein Binding of Compound I

| Species | Mouse | Rat | Dog | Minipig | Human |
|---|---|---|---|---|---|
| Fraction bound [%] | 95.1 | 68.9 | 70.4 | 60.8 | 84.7 |
| Fraction unbound [%] | 4.9 | 31.1 | 29.6 | 39.2 | 15.3 |

In Vitro Metabolic Stability of Compound I in Hepatocyte Incubations

| Species | Mouse | Rat | Dog | Minipig | Human |
|---|---|---|---|---|---|
| CL intrinsic, in vitro [μL/min/10e6 cells] | 16.4 | 8.77 | 3.15 | 2.73 | 4.11 |
| CL, in vivo [mL/min/kg] | 49 | 26 | 14 | 6.8 | 7.9 |

Intravenous Pharmacokinetics of Compound I in Animals

| Species | Mouse | Rat | Dog | Minipig |
|---|---|---|---|---|
| Animal number/gender | n = 2f | n = 2m | n = 3m | n = 1m/1f |
| Intravenous PK parameters (mean values) | | | | |
| IV dose (μmol/kg) | 10 | 5 | 5 | 5 |
| AUC(0-inf) (nM · h) | 1990 | 1490 | 5990 | 4310 |
| CL (mL/min/kg) | 86.0 | 56.1 | 14.0 | 20.0 |
| $V_{ss}$ (L/kg) | 3.29 | 5.04 | 4.94 | 5.07 |
| $MRT_{disp}$ (h) | 0.623 | 1.49 | 6.40 | 4.15 |

Oral Pharmacokinetics of Compound I in Animals

| Species | Mouse | Rat | Dog | Minipig |
|---|---|---|---|---|
| Animal number/gender | n = 3m/0f | n = 3m/0f | n = 3m/0f | n = 3m/0f |
| Oral PK parameters (mean values) | | | | |
| Oral Dose (μmol/kg) | 20 | 20 | 5 | not done |
| $C_{max}$ (nM) | 974 | 580 | 317 | not done |

-continued

| Species | Mouse | Rat | Dog | Minipig |
|---|---|---|---|---|
| $t_{max}$ (h) | 1.00 | 1.50 | 0.917 | not done |
| AUC(0-inf) (nM · h) | 3160 | 2270 | 1500 | not done |
| $MRT_{tot}$ (h) | 3.99 | 5.49 | 5.77 | not done |
| F (%) | 79 | 38 | 25 | Not calculated |

Oral Pharmacokinetics of Citrate Salt 1 in Rats

| Species | Rat |
|---|---|
| Animal number/gender | n = 3m/0f |
| Oral PK parameters $^c$ (mean values) | |
| Oral Dose (μmol/kg) | 20 |
| $C_{max}$ (nM) | 454 |
| $t_{max}$ (h) | 1.08 |
| AUC(0-inf) (nM · h) | 1710 |
| $MRT_{tot}$ (h) | 3.3 |

Inhibition of hERG-Mediated Potassium Current

Compound I inhibited the hERG-mediated potassium current with $IC_{50}$>30 μM (12% inhibition at 10 μM, 28% inhibition at 30 μM).

In Vitro Phospholipidosis Assay

Compound I shows the propensitiy to be phospholipidogenic in the in vitro Phospholipidosis assay; the lowest phospholipidogenic concentration of compound I in this in vitro assay is 200 μM.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of inhibiting CCR2 activity in a patient suffering from pain, comprising administering to the patient in need thereof a therapeutically effective amount of a compound of Formula 1:

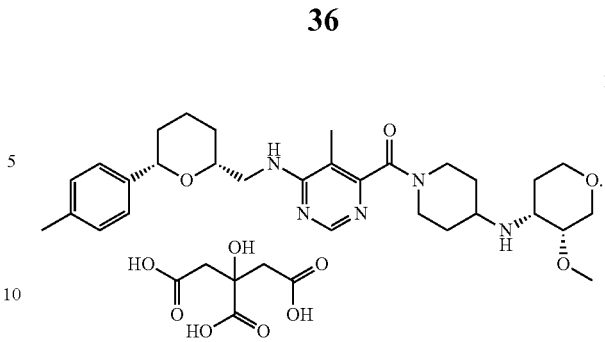

2. The method of claim 1, wherein the pain is inflammatory pain.

3. The method of claim 1, wherein the pain is chronic pain.

4. The method of claim 1, wherein the pain is due to osteoarthritis.

5. The method of claim 1, wherein the compound of Formula 1 is in crystalline form.

6. The method of claim 2, wherein the compound of Formula 1 is in crystalline form.

7. The method of claim 3, wherein the compound of Formula 1 is in crystalline form.

8. The method of claim 4, wherein the compound of Formula 1 is in crystalline form.

9. The method of claim 5, wherein the crystalline form is characterized by a X-ray powder diffraction pattern comprising peaks at the following 2-theta values measured using monochromatic CuKα1 radiation of λ=1.54056 Å, 40 kV, 40 mA: 19.1° and 22.4°.

10. The method of claim 6, wherein the crystalline form is characterized by a X-ray powder diffraction pattern comprising peaks at the following 2-theta values measured using monochromatic CuKα1 radiation of λ=1.54056 Å, 40 kV, 40 mA: 19.1° and 22.4°.

11. The method of claim 7, wherein the crystalline form is characterized by a X-ray powder diffraction pattern comprising peaks at the following 2-theta values measured using monochromatic CuKα1 radiation of λ=1.54056 Å, 40 kV, 40 mA: 19.1° and 22.4°.

12. The method of claim 8, wherein the crystalline form is characterized by a X-ray powder diffraction pattern comprising peaks at the following 2-theta values measured using monochromatic CuKα1 radiation of λ=1.54056 Å, 40 kV, 40 mA: 19.1° and 22.4°.

13. The method of claim 5, wherein the crystalline form exhibits a X-ray powder diffraction pattern comprising peaks at the following 2-theta values measured using monochromatic CuKα1 radiation of λ=1.54056 Å, 40 kV, 40 mA: 12.2±0.2, 13.7±0.2, 14.6±0.2, 19.1±0.2, and 22.4±0.2.

14. The method of claim 6, wherein the crystalline form exhibits a X-ray powder diffraction pattern comprising peaks at the following 2-theta values measured using monochromatic CuKα1 radiation of λ=1.54056 Å, 40 kV, 40 mA: 12.2±0.2, 13.7±0.2, 14.6±0.2, 19.1±0.2, and 22.4±0.2.

15. The method of claim 7, wherein the crystalline form exhibits a X-ray powder diffraction pattern comprising peaks at the following 2-theta values measured using monochromatic CuKα1 radiation of λ=1.54056 Å, 40 kV, 40 mA: 12.2±0.2, 13.7±0.2, 14.6±0.2, 19.1±0.2, and 22.4±0.2.

16. The method of claim 8 wherein the crystalline form exhibits a X-ray powder diffraction pattern comprising peaks at the following 2-theta values measured using monochromatic CuKα1 radiation of λ=1.54056 Å, 40 mA: 12.2±0.2, 13.7±0.2, 14.6±0.2, 19.1±0.2, and 22.4±0.2.

17. The method of claim 5, wherein the crystalline form is characterized by the following X-ray powder diffraction pattern expressed in terms of diffraction angle 2θ, interplanar distances d, and relative intensity (expressed as a percentage with respect to the most intense peak):

| 2-theta [°] | d-value [Å] | Intensity I/I$_0$ [%] |
|---|---|---|
| 4.36 | 20.24 | 17 |
| 12.17 | 7.27 | 41 |
| 12.51 | 7.07 | 6 |
| 13.13 | 6.74 | 7 |
| 13.66 | 6.48 | 39 |
| 14.20 | 6.23 | 14 |
| 14.60 | 6.06 | 32 |
| 15.03 | 5.89 | 5 |
| 15.25 | 5.81 | 4 |
| 15.97 | 5.54 | 11 |
| 16.51 | 5.37 | 13 |
| 17.05 | 5.20 | 13 |
| 17.54 | 5.05 | 4 |
| 17.88 | 4.96 | 5 |
| 18.65 | 4.75 | 22 |
| 19.05 | 4.66 | 100 |
| 19.68 | 4.51 | 11 |
| 20.42 | 4.35 | 6 |
| 20.84 | 4.26 | 4 |
| 21.25 | 4.18 | 3 |
| 21.90 | 4.06 | 5 |
| 22.42 | 3.96 | 92 |
| 23.19 | 3.83 | 9 |
| 23.70 | 3.75 | 16 |
| 24.34 | 3.65 | 4 |
| 24.56 | 3.62 | 23 |
| 24.89 | 3.57 | 16 |
| 25.20 | 3.53 | 7 |
| 25.36 | 3.51 | 7 |
| 25.67 | 3.47 | 6 |
| 26.26 | 3.39 | 23 |
| 26.59 | 3.35 | 12 |
| 27.51 | 3.24 | 6 |
| 27.71 | 3.22 | 6 |
| 28.01 | 3.18 | 7 |
| 28.23 | 3.16 | 5 |
| 28.57 | 3.12 | 3 |
| 29.44 | 3.03 | 12 |
| 30.15 | 2.96 | 4. |

18. The method of claim 6, wherein the crystalline form is characterized by the following X-ray powder diffraction pattern expressed in terms of diffraction angle 2θ, interplanar distances d, and relative intensity (expressed as a percentage with respect to the most intense peak):

| 2-theta [°] | d-value [Å] | Intensity I/I$_0$ [%] |
|---|---|---|
| 4.36 | 20.24 | 17 |
| 12.17 | 7.27 | 41 |
| 12.51 | 7.07 | 6 |
| 13.13 | 6.74 | 7 |
| 13.66 | 6.48 | 39 |
| 14.20 | 6.23 | 14 |
| 14.60 | 6.06 | 32 |
| 15.03 | 5.89 | 5 |
| 15.25 | 5.81 | 4 |
| 15.97 | 5.54 | 11 |
| 16.51 | 5.37 | 13 |
| 17.05 | 5.20 | 13 |
| 17.54 | 5.05 | 4 |
| 17.88 | 4.96 | 5 |
| 18.65 | 4.75 | 22 |
| 19.05 | 4.66 | 100 |
| 19.68 | 4.51 | 11 |
| 20.42 | 4.35 | 6 |
| 20.84 | 4.26 | 4 |
| 21.25 | 4.18 | 3 |
| 21.90 | 4.06 | 5 |
| 22.42 | 3.96 | 92 |
| 23.19 | 3.83 | 9 |
| 23.70 | 3.75 | 16 |
| 24.34 | 3.65 | 4 |
| 24.56 | 3.62 | 23 |
| 24.89 | 3.57 | 16 |
| 25.20 | 3.53 | 7 |
| 25.36 | 3.51 | 7 |
| 25.67 | 3.47 | 6 |
| 26.26 | 3.39 | 23 |
| 26.59 | 3.35 | 12 |
| 27.51 | 3.24 | 6 |
| 27.71 | 3.22 | 6 |
| 28.01 | 3.18 | 7 |
| 28.23 | 3.16 | 5 |
| 28.57 | 3.12 | 3 |
| 29.44 | 3.03 | 12 |
| 30.15 | 2.96 | 4. |

19. The method of claim 7, wherein the crystalline form is characterized by the following X-ray powder diffraction pattern expressed in terms of diffraction angle 2θ, interplanar distances d, and relative intensity (expressed as a percentage with respect to the most intense peak):

| 2-theta [°] | d-value [Å] | Intensity I/I$_0$ [%] |
|---|---|---|
| 4.36 | 20.24 | 17 |
| 12.17 | 7.27 | 41 |
| 12.51 | 7.07 | 6 |
| 13.13 | 6.74 | 7 |
| 13.66 | 6.48 | 39 |
| 14.20 | 6.23 | 14 |
| 14.60 | 6.06 | 32 |
| 15.03 | 5.89 | 5 |
| 15.25 | 5.81 | 4 |
| 15.97 | 5.54 | 11 |
| 16.51 | 5.37 | 13 |
| 17.05 | 5.20 | 13 |
| 17.54 | 5.05 | 4 |
| 17.88 | 4.96 | 5 |
| 18.65 | 4.75 | 22 |
| 19.05 | 4.66 | 100 |
| 19.68 | 4.51 | 11 |
| 20.42 | 4.35 | 6 |
| 20.84 | 4.26 | 4 |
| 21.25 | 4.18 | 3 |
| 21.90 | 4.06 | 5 |
| 22.42 | 3.96 | 92 |
| 23.19 | 3.83 | 9 |
| 23.70 | 3.75 | 16 |
| 24.34 | 3.65 | 4 |
| 24.56 | 3.62 | 23 |
| 24.89 | 3.57 | 16 |
| 25.20 | 3.53 | 7 |
| 25.36 | 3.51 | 7 |
| 25.67 | 3.47 | 6 |
| 26.26 | 3.39 | 23 |
| 26.59 | 3.35 | 12 |
| 27.51 | 3.24 | 6 |
| 27.71 | 3.22 | 6 |
| 28.01 | 3.18 | 7 |
| 28.23 | 3.16 | 5 |
| 28.57 | 3.12 | 3 |
| 29.44 | 3.03 | 12 |
| 30.15 | 2.96 | 4. |

20. The method of claim 8, wherein the crystalline form is characterized by the following X-ray powder diffraction pattern expressed in terms of diffraction angle 2θ, interplanar distances d, and relative intensity (expressed as a percentage with respect to the most intense peak):

| 2-theta [°] | d-value [Å] | Intensity I/I₀ [%] |
| --- | --- | --- |
| 4.36 | 20.24 | 17 |
| 12.17 | 7.27 | 41 |
| 12.51 | 7.07 | 6 |
| 13.13 | 6.74 | 7 |
| 13.66 | 6.48 | 39 |
| 14.20 | 6.23 | 14 |
| 14.60 | 6.06 | 32 |
| 15.03 | 5.89 | 5 |
| 15.25 | 5.81 | 4 |
| 15.97 | 5.54 | 11 |
| 16.51 | 5.37 | 13 |
| 17.05 | 5.20 | 13 |
| 17.54 | 5.05 | 4 |
| 17.88 | 4.96 | 5 |
| 18.65 | 4.75 | 22 |
| 19.05 | 4.66 | 100 |
| 19.68 | 4.51 | 11 |
| 20.42 | 4.35 | 6 |
| 20.84 | 4.26 | 4 |
| 21.25 | 4.18 | 3 |
| 21.90 | 4.06 | 5 |
| 22.42 | 3.96 | 92 |
| 23.19 | 3.83 | 9 |
| 23.70 | 3.75 | 16 |
| 24.34 | 3.65 | 4 |
| 24.56 | 3.62 | 23 |
| 24.89 | 3.57 | 16 |
| 25.20 | 3.53 | 7 |
| 25.36 | 3.51 | 7 |
| 25.67 | 3.47 | 6 |
| 26.26 | 3.39 | 23 |
| 26.59 | 3.35 | 12 |
| 27.51 | 3.24 | 6 |
| 27.71 | 3.22 | 6 |
| 28.01 | 3.18 | 7 |
| 28.23 | 3.16 | 5 |
| 28.57 | 3.12 | 3 |
| 29.44 | 3.03 | 12 |
| 30.15 | 2.96 | 4. |

\* \* \* \* \*